(12) United States Patent
Tate et al.

(10) Patent No.: US 8,574,560 B2
(45) Date of Patent: Nov. 5, 2013

(54) HAIR STYLING METHOD

(75) Inventors: Yoshimasa Tate, Sumida-ku (JP); Koji Yui, Sumida-ku (JP); Michiko Asami, Chuo-ku (JP)

(73) Assignee: KAO Corporation, Tokyo (JP)

( * ) Notice: Subject to any disclaimer, the term of this patent is extended or adjusted under 35 U.S.C. 154(b) by 132 days.

(21) Appl. No.: 12/993,772

(22) PCT Filed: May 21, 2009

(86) PCT No.: PCT/JP2009/002245
§ 371 (c)(1),
(2), (4) Date: Nov. 19, 2010

(87) PCT Pub. No.: WO2009/142020
PCT Pub. Date: Nov. 26, 2009

(65) Prior Publication Data
US 2011/0067721 A1 Mar. 24, 2011

(30) Foreign Application Priority Data

May 21, 2008 (JP) ................................. 2008-132698
May 21, 2008 (JP) ................................. 2008-132699

(51) Int. Cl.
| | | |
|---|---|---|
| A61K 8/72 | (2006.01) |
| A61Q 5/02 | (2006.01) |
| A61Q 5/06 | (2006.01) |
| C08F 226/02 | (2006.01) |
| C08F 236/02 | (2006.01) |
| C08F 20/56 | (2006.01) |
| A61K 8/04 | (2006.01) |
| C08F 22/10 | (2006.01) |
| C08F 22/38 | (2006.01) |

(52) U.S. Cl.
CPC . *A61Q 5/02* (2013.01); *A61K 8/046* (2013.01); *A61K 8/72* (2013.01); *A61Q 5/06* (2013.01); *C08F 226/02* (2013.01); *C08F 236/02* (2013.01); *C08F 20/56* (2013.01); *C08F 22/10* (2013.01); *C08F 22/38* (2013.01)
USPC ..... 424/70.1; 132/203; 424/70.16; 424/70.17

(58) Field of Classification Search
None
See application file for complete search history.

(56) References Cited

U.S. PATENT DOCUMENTS

| 3,954,960 A | * | 5/1976 | Valan ................................ 424/47 |
| 4,240,450 A | | 12/1980 | Grollier et al. |
| 5,180,580 A | | 1/1993 | Hallloran et al. |
| 5,472,689 A | * | 12/1995 | Ito ............................ 424/70.122 |
| 5,663,261 A | * | 9/1997 | Hori et al. .................. 526/307.2 |
| 2005/0063916 A1 | | 3/2005 | Ishii et al. |

FOREIGN PATENT DOCUMENTS

| CN | 1135498 A | 11/1996 |
| EP | 0524612 A2 | 7/1992 |
| EP | 0524612 A3 | 7/1992 |
| JP | 53 139734 | 12/1978 |
| JP | 2 180911 | 7/1990 |
| JP | 4-82819 A | 3/1992 |
| JP | 4-261114 A | 9/1992 |
| JP | 5-25025 | 2/1993 |
| JP | 5-97636 A | 4/1993 |
| JP | 5 255052 | 10/1993 |
| JP | 7 133212 | 5/1995 |
| JP | 7 285832 | 10/1995 |
| JP | 7 309726 | 11/1995 |
| JP | 8-217647 A | 8/1996 |
| JP | 8 291206 | 11/1996 |
| JP | 9 143037 | 6/1997 |
| JP | 9 255534 | 9/1997 |
| JP | 10 1425 | 1/1998 |
| JP | 10 152423 | 6/1998 |
| JP | 10 236550 | 9/1998 |
| JP | 11-35433 A | 2/1999 |
| JP | 11-116443 A | 4/1999 |
| JP | 11 181029 | 7/1999 |
| JP | 2000-226318 A | 8/2000 |
| JP | 2001 48734 | 2/2001 |
| JP | 2002 521412 | 7/2002 |
| JP | 2005 68134 | 3/2005 |
| JP | 2007-326805 | 12/2007 |
| JP | 2009 7347 | 1/2009 |
| JP | 2009 23963 | 2/2009 |
| JP | 2009 40755 | 2/2009 |
| WO | 01 10397 | 2/2001 |

OTHER PUBLICATIONS

MG Brookins. "The Action of Hair Sprays on Hair." Journal of the Society of Cosmetic Chemists, vol. 16, 1965, pp. 309-315.*
International Search Report issued Aug. 25, 2009 in PCT/JP09/002245 filed May 21, 2009.
Office Action issued Dec. 26, 2011, in Chinese Patent Application No. 200980116733.9 (with English-language translation).
Chinese Office Action Issued Oct. 10, 2012 in Patent Application No. 200980116733.9 (with English translation).

* cited by examiner

*Primary Examiner* — Frederick Krass
*Assistant Examiner* — Isaac Shomer
(74) *Attorney, Agent, or Firm* — Oblon, Spivak, McClelland, Maier & Neustadt, L.L.P.

(57) ABSTRACT

A hair styling method including:
(A) increasing the number of intersections of hair fibers, thereby enhancing the volume of the hair; and
(B) applying an aerosol hair cosmetic composition capable of forming a film having a film strength, as measured by a film strength evaluation method, of 800 gf/cm$^2$ or greater.

12 Claims, 3 Drawing Sheets

(A)

(B)

Example of a space volume surrounded by hair fibers

When hair fibers are arranged as in (A), the space surrounded by these hair fibers is as shown by the shaded portion in FIG. (B). To facilitate understanding, the actual three-dimensional state of fibers is illustrated two-dimensionally.

Hair fibers arranged so that the long-axis directions thereof be the same.

Hair fibers arranged so that the long-axis directions thereof be perpendicular to each other.

HAIR STYLING METHOD

CROSS REFERENCE TO RELATED APPLICATION

This application is a 371 of PCT/JP09/002245, filed on May 21, 2009, and claims priority to the following Japanese Patent Applications: 2008-132698, filed on May 21, 2008; and 2008-132699, filed on May 21, 2008.

FIELD OF THE INVENTION

The present invention relates to a hair styling method capable of retaining a hair style with a fluffy finish for a long period; and a hair cosmetic composition excellent in hair styling performance and wash-off property.

BACKGROUND OF THE INVENTION

Most of aerosol hair cosmetic compositions set hair by making use of the fixing force of a film-forming polymer contained therein. Although such hair cosmetic compositions exhibit sufficient hair styling performance, they undesirably impart stickiness, coarseness, or stiffness to the finished hair. In addition, they cannot keep a fluffy finish for long hours.

Patent Document 1 describes a keratin-substance treating composition containing an anionic polymer and a cationic polymer. The composition can also be used for hair. The composition used as a hair styling agent exhibits sufficient styling performance, but is inferior in wash-off property with a shampoo.

Patent Document 1: JP-A-S53-139734

SUMMARY OF THE INVENTION

The present invention relates to a hair styling method capable of retaining a hair style with a fluffy finish for a long period. The present invention also relates to a hair cosmetic composition excellent in hair styling performance and wash-off property.

The present inventors have found that a hair style with a fluffy finish can be retained for long hours by increasing the number of intersections of hair fibers to enhance the hair volume and by applying a specific aerosol hair cosmetic composition.

The present invention relates to provision of a hair styling method including (A) increasing the number of intersections of hair fibers to enhance the volume of hair, and (B) applying an aerosol hair cosmetic composition capable of forming a film having a film strength, as measured by a film strength evaluation method, of 800 gf/cm² or greater.

The present inventors have also found that a hair cosmetic composition excellent in hair styling performance and wash-off property, free from stickiness or coarseness, and capable of forming a fluffy and voluminous hair style by using a specific film-forming copolymer and an anionic film-forming polymer in combination.

The present invention relates to provision of an aerosol hair cosmetic composition containing the following component (C) and component (D) at a mass ratio (D)/(C) of from 0.1 to 100:

(C) at least one copolymer selected from the following (C1) and (C2):
(C1) copolymers each composed of:
(a) from 30 to 80 mass % of a (meth)acrylamide monomer represented by the following formula (1):

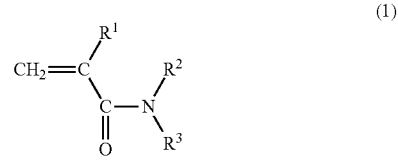

(wherein, $R^1$ represents a hydrogen atom or a methyl group, $R^2$ and $R^3$ may be the same or different and each represents a hydrogen atom or an alkyl group having from 4 to 12 carbon atoms, with the proviso that both $R^2$ and $R^3$ do not represent a hydrogen atom), (b) from 2 to 50 mass % of a (meth)acrylamide monomer represented by the following formula (2):

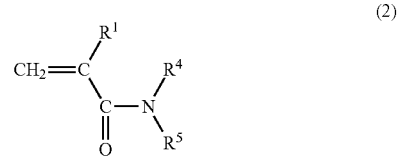

(wherein, $R^1$ has the same meaning as described above, $R^4$ and $R^5$ may be the same or different and each represents a hydrogen atom or an alkyl group having from 1 to 3 carbon atoms), (c) from 0 to 30 mass % of a (meth)acrylic acid ester monomer or a (meth)acrylamide monomer represented by the following formula (3):

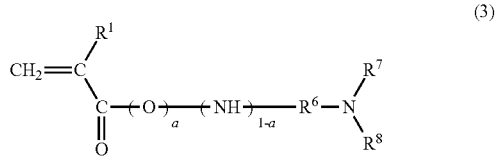

(wherein, $R^1$ has the same meaning as described above, $R^6$ represents an alkylene group having 2 or 3 carbon atoms, $R^7$ and $R^8$ may be the same or different and each represents a methyl group or an ethyl group, and a represents a number of 0 or 1), and (d) from 0 to 40 mass % of a (meth)acrylic acid ester monomer represented by the following formula (4):

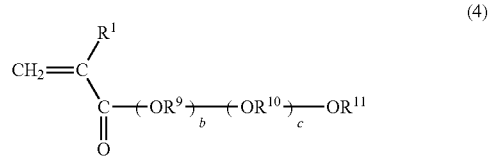

(wherein, $R^1$ has the same meaning as described above, $R^9$ and $R^{10}$ may be the same or different and each represents an alkylene group having from 2 to 4 carbon atoms, $R^{11}$ represents a hydrogen atom, an alkyl group having from 1 to 10 carbon atoms, or a phenyl group, and b and c each represents a number from 0 to 50, with the proviso that both b and c do not stand for 0), and (C2) copolymers each composed of:

(a) from 30 to 80 mass % of a (meth)acrylamide monomer represented by the following formula (5):

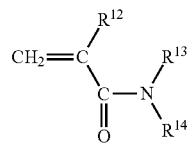

(wherein, $R^{12}$ represents a hydrogen atom or a methyl group, $R^{13}$ and $R^{14}$ may be the same or different and each represents a hydrogen atom or an alkyl group having from 4 to 12 carbon atoms or $R^{13}$ and $R^{14}$ are coupled to each other to form a ring together with a nitrogen atom adjacent thereto), (b) from 5 to 45 mass % of a (meth)acrylic acid ester monomer represented by the following formula (6):

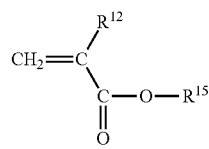

(wherein, $R^{12}$ has the same meaning as described above and $R^{15}$ represents an alkyl group having from 1 to 4 carbon atoms), (c) from 2 to 30 mass % of a (meth)acrylic acid ester monomer or a (meth)acrylamide monomer represented by the following formula (7):

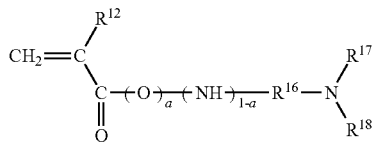

(wherein, $R^{12}$ has same the meaning as described above, $R^{16}$ represents an alkylene group having 2 or 3 carbon atoms, $R^{17}$ and $R^{18}$ may be the same or different and each represents a methyl group or an ethyl group, and a represents a number of 0 or 1), and (d) from 0 to 30 mass % of a (meth)acrylic acid ester monomer represented by the following formula (8):

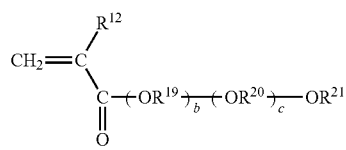

(wherein, $R^{12}$ has the same meaning as described above, $R^{19}$ and $R^{20}$ may be the same or different and each represents an alkylene group having from 2 to 4 carbon atoms, $R^{21}$ represents a hydrogen atom or a methyl group, and b and c each represents a number from 0 to 50 with the proviso that both b and c do not stand for 0), and (D) an anionic film-forming polymer.

EFFECT OF THE INVENTION

According to the present invention, a hair styling performance is excellent and a hair style with fluffy finish can be retained for a long period. In addition, the hair cosmetic composition of the present invention is excellent in hair styling performance and wash-off property, free from stickiness and coarseness, and capable of forming a fluffy and voluminous hair style.

DETAILED DESCRIPTION OF THE INVENTION

In order to effectively create a beautiful hair style, it is necessary in the present invention to (A) increase the number of intersections of hair fibers, thereby enhancing the volume of the hair.

Figure 1:
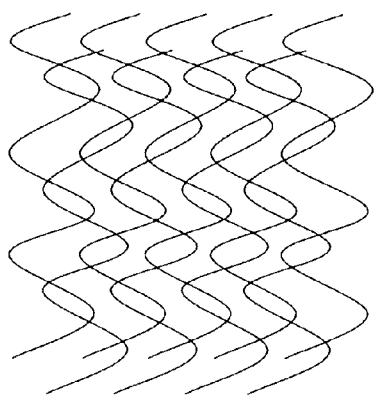
FIG. 1 is a view illustrating a space volume surrounded by hair fibers.
Figure 1:
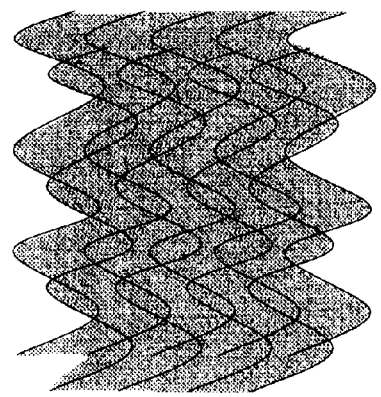

The term "enhancing the volume of the hair" as used herein means increasing the volume of a space surrounded by hair fibers, which is illustrated two-dimensionally in FIG. 1 by a shaded region.

Figure 2:
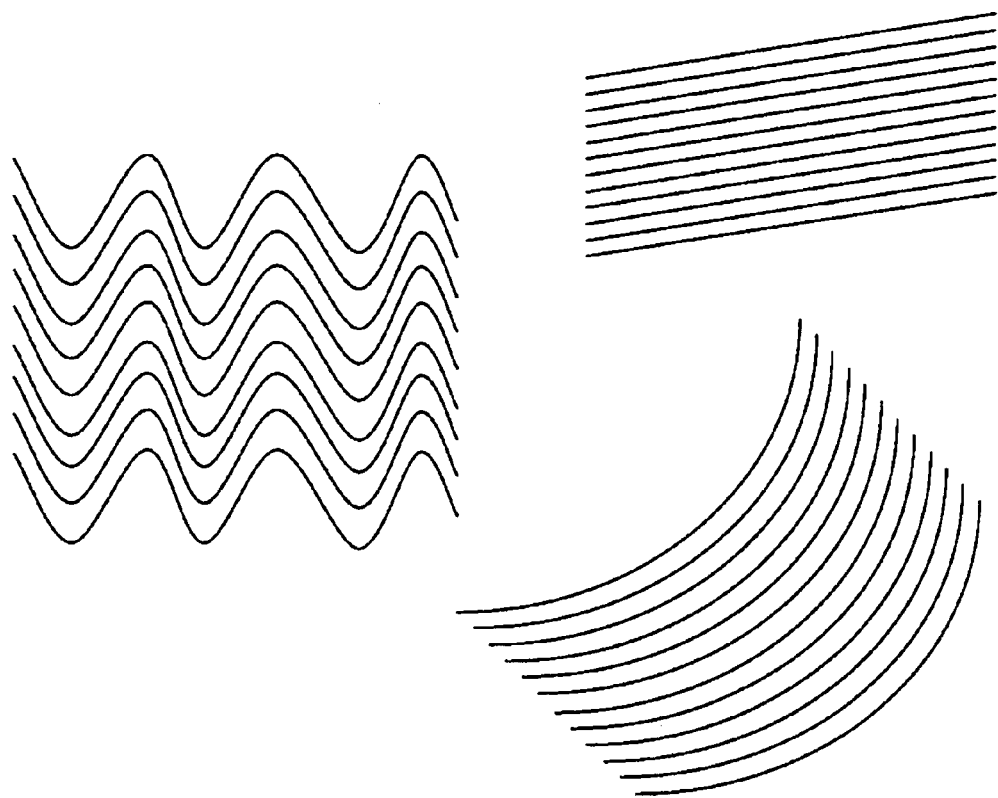
FIG. 2 is a view illustrating hair fibers arranged so that the long-axis directions thereof be the same.
Figure 3:
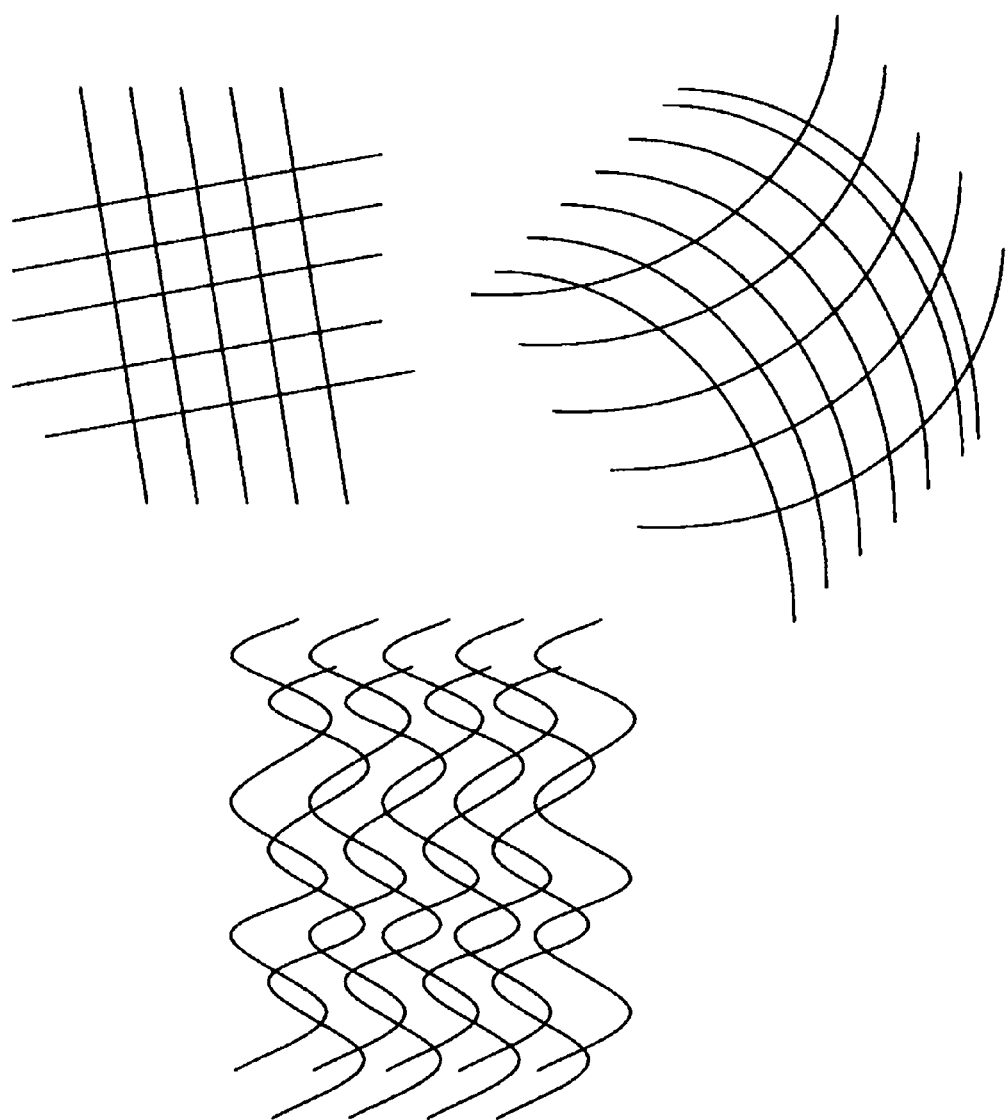
FIG. 3 is a view illustrating hair fibers arranged so that the long-axis directions thereof be perpendicular to each other.

When hair fibers arranged so that the long-axis directions thereof be the same (FIG. 2) and hair fibers arranged so that the long-axis directions thereof be perpendicular to each other (FIG. 3) are cited as extreme examples, actual hair is usually under a state between these two extreme examples. The term "increase the number of intersections" as used herein means a change of the hair state from FIG. 2 to FIG. 3. The concept of increasing the number of intersections includes even a slight change of the state from FIG. 2 to FIG. 3 and it also includes a change of the state to an intermediate one between them.

By increasing the number of intersections, it is possible to effectively enhance the volume of the hair, thereby creating a beautiful hair style with a fluffy finish.

In addition, it is possible to enjoy the thus-made hair style for a long period by (B) applying thereto an aerosol hair cosmetic composition capable of forming a film having a film strength, as measured by a film strength evaluation method, of 800 gf/cm² or greater.

<Method of Increasing the Number of Intersections of Hair Fibers, Thereby Enhancing Hair Volume>

The term "hair" as used herein may mean any of straight hair, unruly hair, straight hair reformed by perming (curly hair or wavy hair), or unruly hair straightened by straight perming. It may be either wetted with water or dried, and dried hair is preferred. It may be either hair to which a hair care agent or treatment has been applied in advance or to which no such an agent has been applied. It may be either dyed or undyed. Further, the length of the hair is not limited and the hair, which is not tied or bundled, may have any length ranging from short hair not reaching ears, eyebrows, or neck to long hair reaching below the chest or waist.

The following are specific examples of increasing the number of intersections of hair fibers, thereby enhancing hair volume.

(1) Change the long-axis direction of hair fibers from a fixed direction to more random directions by combing or teasing (generally called "backcombing") them with a comb, brush, or fingers from the tips towards the roots.

(2) Form a bundle of hair at a position as near as possible to the root thereof (gather preferably at a position higher than ears) and secure it with a hair pin or fasten it with an elastic band so as to prevent the stray hair. Then, change the long-axis directions of hair fibers, which are nearer to the tips in relation to the gathered position, from one direction to various directions with fingers, a comb, or a brush (so-called "scatter"). Alternatively, backcombing of the hair fibers, which are nearer to the tips in relation to the gathered position, is also recommendable. In this case, the bundled position is not limited and it may be any of the top, back, or side portion of the head. The number of the hair bundles is also not limited.

(3) Curl or wave hair with a hair iron or hair curler. Separate the resulting curled or waved hair into individual fibers with fingers to change the long-axis directions thereof to various directions. Alternatively, backcombing of the curled hair prior to separation of it into individual fibers with fingers is also recommended. A portion of the hair to be curled may be either a portion of the hair nearer the tip in relation to the bundled position of the hair or a portion of the hair hung down without bundling or binding. The curled position may be any of the top, back, or side of the head, above or below the ears.

These methods (1) to (3) may be used either alone or in combination, or they may be used in combination with another hair styling method.

We can retain and enjoy a beautiful hair style for a long period by using such a method of increasing the number of intersections of hair fibers and (B) applying an aerosol hair cosmetic composition capable of forming a film having a film strength, as measured by a film strength evaluation method, of 800 gf/cm² or greater.

In the aerosol hair cosmetic composition (B), on the other hand, a film strength, as measured by the evaluation method described below, of 800 gf/cm² or greater, preferably 1000 gf/cm² or greater, more preferably 1500 gf/cm² or greater, even more preferably 2000 gf/cm2 or greater, even more preferably 2300 gf/cm² or greater. When the film strength falls within this range, a hair style with a fluffy finish can be retained for long hours. The film strength, as measured by the evaluation method, is, on the other hand, preferably 8000 gf/cm² or less, more preferably 6000 gf/cm² or less, even more preferably 5000 gf/cm² or less, even more preferably 4000 gf/cm² or less. The film strength falling within these ranges makes it possible to provide the hair to which the composition is applied with a good feel.

The film strength is measured in accordance with the following evaluation method.

<Preparation of Sample>

(1) Spray an aerosol hair cosmetic composition to a container, stir it for 2 hours with a stirrer, and collect, as a stock solution, the composition from which a propellant has been removed (this operation is omitted if the stock solution is available directly). Put 15 g of the stock solution thus collected in a Petri dish having a diameter of 7.5 cm (preferably, that made of a material, for example, Teflon (trade mark) facilitating separation of a film from the dish) and evaporate it at 25° C. and 65% Rh for 3 days to dryness.

(2) Put the Petri dish having the stock solution therein in a constant-temperature box set at 25° C. and 98% Rh for 30 minutes.

(3) Separate the softened film from the Petri dish with a spatel or the like.

(4) Repeat the operations (2) and (3) if the film cannot be separated.

(5) Cut the film into pieces of 3.0 mm×30.0 mm.

(6) Lay them on a sheet made of a material to which the film is less apt to adhere such as Teflon (trade mark), overlay a sheet made of a material to which the film is less apt to adhere such as plastic sheet, and put a weight on the plastic sheet to prevent the film from warping during drying.

(7) One day later, measure the thickness of the film at the center portion thereof with a thickness gauge ("SMD-565", product of TECLOCK Corporation) (N=5).

<Measurement of Breaking Strength of Sample>

(1) Allow the film pieces to stand for 2 hours in a constant-temperature box set at 20° C. and 98% Rh.

(2) Take out the film pieces from the temperature-constant box and measure the film breaking strength by using a tensile and compression testing machine ("TMD-200N", product of Minebea Co., Ltd.) (chuck to chuck distance: 2 cm, sample length between chucks: 0.5 cm, pulling rate: 200 mm/min).

(3) Calculate the cross-sectional area of the film based on the thickness of the film measured previously.

(4) Calculate a rupture stress by dividing the film breaking strength with the cross-sectional area (N=5) and define it as a film strength.

Such a hair cosmetic composition contains a film-forming polymer. The film-forming polymer may be any of a synthetic polymer, a natural polymer, and a modified natural polymer. It may have any electrostatic property, that is, may be any of anionic, amphoteric, cationic, or nonionic. These polymers may be used either alone or as a mixture of two or more thereof. The term "film-forming polymer" as used herein means a polymer having a breaking strength, as measured by the evaluation method described below, of 100 gf/cm² or greater, preferably 200 gf/cm² or greater, more preferably 300 gf/cm² or greater.

Evaluation Method:

The breaking strength of a specific polymer to be evaluated is evaluated in a manner similar to that employed in the film strength evaluation method except that 15 g of the polymer dissolved in ethanol to give a film thickness of from 200 to 400 μm is put in a Petri dish having a diameter of 7.5 cm (preferably, a Petri dish made of a material facilitating film separation such as Teflon (trade mark)) and is evaporated for 3 days at 25° C. and 65% Rh to dryness.

Examples of the film-forming polymer are described below.

<Anionic Film-Forming Polymer>

Anionic film-forming polymers having, as a structural unit thereof, any of crotonic acid, maleic acid, maleic acid monoester, and itaconic acid:

Although no limitation is imposed insofar as it has, as a structural unit thereof, any of crotonic acid, maleic acid, maleic acid monoester, and itaconic acid, those obtained by copolymerization with at least one of vinyl ethers, vinyl esters, and vinyl alcohols are preferred; methyl vinyl ether/alkyl maleate copolymers (such as "Gantrez ES-225", "Gantrez ES-425", and "Gantrez SP-215", each product of ISP), vinyl acetate/crotonic acid copolymers (such as "Resyn 28-1310", product of National Starch), vinyl acetate/crotonic acid/vinyl neodecanoate copolymers (such as "Resyn 28-2930", product of National Starch), vinyl acetate/crotonic acid/vinyl propionate copolymers (such as "Luviset CAP", product of BASF), and vinyl alcohol/itaconic acid copolymers (such as "KM-118", product of Kuraray) are more preferred; and methyl vinyl ether/alkyl maleate copolymers, vinyl acetate/crotonic acid copolymers, vinyl acetate/crotonic acid/vinyl neodecanoate copolymers, and vinyl acetate/crotonic acid/vinyl propionate copolymers are even more preferred.

Anionic film-forming polymers having, as a structural unit thereof, (meth)acrylic acid:

Although no limitation is imposed insofar it is a vinyl polymer having, as a structural unit thereof, (meth)acrylic acid, copolymers with at least one of alkyl (meth)acrylates and N-alkyl(meth)acrylamides are preferred.

More preferred examples include acrylic acid/ethyl acrylate/N-t-butyl acrylamide copolymers (such as "Ultrahold 8" and "Ultrahold Strong", each product of BASF), octyl acrylamide/acrylic acid copolymers (such as "Amphomer V-42", product of National Starch), acrylate/methacrylate/acrylic acid/methacrylic acid copolymers (such as "Amerhold DR25", product of Union Carbide), acrylates/diacetoneacrylamide copolymers (such as "Pluscize L9540B", product of Goo Chemical (neutralized product of this polymer with 2-amino-2-methyl-1-propyl alcohol)), and acrylates/$C_{1-18}$ alkyl acrylates/$C_{1-8}$ alkylacrylamide copolymers (such as "Pluscize L9909B", product of Goo Chemical (neutralized product of this polymer with 2-amino-2-methyl-1-propyl alcohol)), with acrylate/methacrylate/acrylic acid/methacrylic acid copolymers, acrylates/diacetoneacrylamide copolymers, and acrylates/$C_{1-18}$ alkyl acrylates/$C_{1-8}$ alkylacrylamide copolymers being more preferred.

Natural anionic film-forming polymers having either one of a carboxyl group or a sulfuric acid group:

Although no limitation is imposed insofar as it is a natural polysaccharide having either a carboxyl group or a sulfuric acid group. Preferred examples include carrageenan (such as "Soageena LX22" and "Soageena ML210", product of Mitsubishi Rayon) and xanthan gum (such as "ECHO gum T", product of Dainippon Sumitomo Pharma Co., Ltd.), with carrageenan being more preferred.

Polyesters having either one of a carboxyl group or a sulfonic acid group:

Although there is no particular limitation, water dispersible polyesters (such as "AQ38S" and "AQ55S", product of Eastman Kodak) are preferred.

As the anionic film-forming polymer, methyl vinyl ether/alkyl maleate copolymers, acrylates/diacetoneacrylamide copolymers, and acrylates/$C_{1-18}$ alkyl acrylates/$C_{1-8}$ alkylacrylamide copolymers.

<Amphoteric Film-Forming Polymers>

Although no particular limitation is imposed, synthetic polymers are preferred, with vinyl polymers being more preferred. The term "amphoteric polymer" as used herein means a polymer containing both a copolymer having, as a structural unit thereof, at least one anionic monomer and at least one cationic monomer and a copolymer having, as a structural unit thereof, at least one betaine monomer having, in the monomer structure thereof, both an anionic portion and a cationic portion.

Of these, dimethyl diallyl ammonium/acrylamide/acrylic acid copolymers (such as "Merquat 3331", product of Calgon), N-methacryloyloxyethyl-N,N-dimethylammonium-α-N-methylcarboxybetaine/alkyl methacrylate copolymers "Yukaformer M-75" and "Yukaformer SM", each product of Mitsubishi Chemical), and octylacrylamide/acrylate/butylaminoethyl methacrylate copolymers ("Amphomer 28-4910", product of National Starch) are preferred, with octylacrylamide/acrylate/butylaminoethyl methacrylate copolymers being more preferred.

<Cationic Film-Forming Polymers>

Although there is no particular limitation, preferred examples include vinyl polymers having at least one of a quaternary ammonium structure, a tertiary amine structure, a secondary amine structure, and a primary amine structure, and natural polysaccharides having a quaternary ammonium structure, a tertiary amine structure, a secondary amine structure, or a primary amine structure, or modified products of natural polysaccharides.

Vinyl Polymer:

Examples include vinyl polymers having, as a structural unit thereof, at least one selected from (meth)acrylic acid esters having a secondary amino group, a tertiary amino group, or a quaternary ammonium group, (meth)acrylamides having a secondary amino group, a tertiary amino group, or a quaternary ammonium group, N-substituted allylamines, and N-substituted allylammoniums. Of these, preferred are alkylacrylamide/acrylate/alkylaminoalkylacrylamide/polyethylene glycol methacrylate copolymers (polymers described in Examples of JP-A-H02-180911), alkylacrylamide/alkylaminoalkylacrylamide/polyethylene glycol methacrylate copolymers (polymers described in Examples of JP-A-H08-291206), polydimethyldiallylammonium chlorides (such as "Merquat 100", product of Calgon), acylamidopropyltrimethylammonium chloride/acrylate copolymers (such as "Merquat", product of Calgon), acrylamide/dimethyldiallylammonium chloride copolymers (such as "Merquat 550" and "Merquat 2200", product of Calgon), methylvinylimidazolium chloride/vinylpyrrolidone copolymers (such as "Luviquat FC370", "Luviquat FC550", "Luviquat FC905", and "Luviquat HM552", each product of BASF), vinylpyrrolidone/dimethylaminopropylmethacrylamide copolymers (such as "Guffquat HS-100", product of ISP), diethyl sulfate salts of vinylpyrrolidone/dimethylaminoethyl methacrylate copolymers (such as "Guffquat 734", "Guffquat 755N", and "Guaffquat 755", each product of ISP), vinyl alcohol/dimethylaminopropylmethacrylamide copolymers (such as "C-318", product of Kuraray), vinylpyrrolidone/dimethylaminoethyl methacrylate copolymers (such as "Copolymer 845", "Copolymer 937", and "Copolymer 958", each product of ISP), vinylpyrrolidone/alkylaminoacrylate/vinyl caprolactam copolymers (such as "Copolymer VC-713", product of ISP), and vinyl alcohol/vinylamine copolymers (such as "VA-120-HCl", product of Air Products).

Natural polysaccharides or modified products thereof:

Preferred examples include hydroxyethyl cellulose/dimethyldiallylammonium chloride copolymers (such as "Celquat H-100" and "Celquat L-200", each product of National Starch), hydroxyethyl cellulose/2-hydroxypropyltrimethylammonium chloride (such as "Polymer JR-400", product of Union Carbide), guar hydroxypropyltrimonium chloride (such as "Cosmedia Guar C261N", product of Henkel and "Jaguar C-17", product of Rhone-Poulenc Inc), hydroxypropylchitosan (such as "Chitofilmer HV-10", product of Ichimaru Pharcos)), and chitosan-dl-pyrrolidonecarboxylate salts (such as "Kytamer PC", trade name, product of Union Carbide), with hydroxyethyl cellulose/dimethyldiallylammonium chloride copolymers (such as "Celquat H-100" and "Celquat L-200", each product of National Starch), hydroxyethyl cellulose/2-hydroxypropyltrimethylammonium chloride (such as "Polymer JR-400", product of Union Carbide), and guar hydroxypropyltrimonium chloride (such as "Cosmedia Guar C261N", product of Henkel and "Jaguar C-17", product of Rhone-Poulenc Inc) being more preferred.

Of the cationic film-forming polymers, alkylacrylamide/acrylate/alkylaminoalkylacrylamide/polyethylene glycol methacrylate copolymers and alkylacrylamide/alkylaminoalkylacrylamide/polyethylene glycol methacrylate copolymers are more preferred.

Of these film-forming polymers, at least one copolymer selected from (B1) and (B2) are more preferred.

(B1) copolymers each composed of:
(a) from 30 to 80 mass % of a (meth)acrylamide monomer represented by the following formula (1):

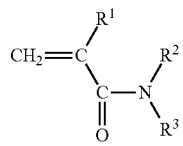

(1)

(wherein, $R^1$ represents a hydrogen atom or a methyl group, $R^2$ and $R^3$ may be the same or different and each represents a hydrogen atom or an alkyl group having from 4 to 12 carbon atoms, with the proviso that both $R^2$ and $R^3$ do not represent a hydrogen atom), (b) from 2 to 50 mass % of a (meth)acrylamide monomer represented by the following formula (2):

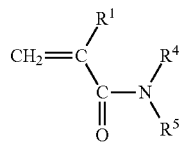

(2)

(wherein, $R^1$ has the same meaning as described above, $R^4$ and $R^5$ may be the same or different and each represents a hydrogen atom or an alkyl group having from 1 to 3 carbon atoms), (c) from 0 to 30 mass % of a (meth)acrylic acid ester monomer or a (meth)acrylamide monomer represented by the following formula: (3):

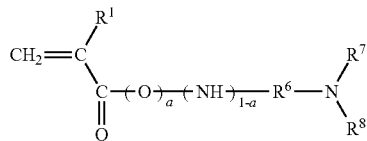

(3)

(wherein, $R^1$ has the same meaning as described above, $R^6$ represents an alkylene group having 2 or 3 carbon atoms, $R^7$ and $R^8$ may be the same or different and each represents a methyl group or an ethyl group, and a represents a number of 0 or 1), and (d) from 0 to 40 mass % of a (meth)acrylic acid ester monomer represented by the following formula (4):

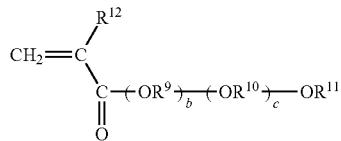

(4)

(wherein, $R^1$ has the same meaning as described above, $R^9$ and $R^{10}$ may be the same or different and each represents an alkylene group having from 2 to 4 carbon atoms, $R^{11}$ represents a hydrogen atom, an alkyl group having from 1 to 10 carbon atoms, or a phenyl group, and b and c each represents a number from 0 to 50, with the proviso that both b and c do not stand for 0), and (B2) copolymers each composed of:
(a) from 30 to 80 mass % of a (meth)acrylamide monomer represented by the following formula (5):

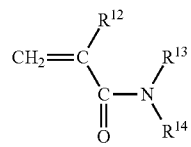

(5)

(wherein, $R^{12}$ represents a hydrogen atom or a methyl group, $R^{13}$ and $R^{14}$ may be the same or different and each represents a hydrogen atom or an alkyl group having from 4 to 12 carbon atoms or $R^{13}$ and $R^{14}$ are coupled to each other to form a ring together with a nitrogen atom adjacent thereto), (b) from 5 to 45 mass % of a (meth)acrylic acid ester monomer represented by the following formula (6):

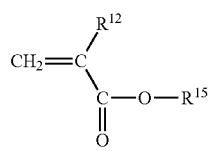

(6)

(wherein, $R^{12}$ has the same meaning as described above and $R^{15}$ represents an alkyl group having from 1 to 4 carbon atoms), (c) from 2 to 30 mass % of a (meth)acrylic acid ester monomer or a (meth)acrylamide monomer represented by the following formula (7):

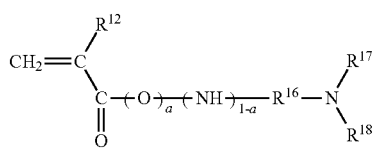

(7)

(wherein, $R^{12}$ has same the meaning as described above, $R^{16}$ represents an alkylene group having 2 or 3 carbon atoms, $R^{17}$ and $R^{18}$ may be the same or different and each represents a methyl group or an ethyl group, and a represents a number of 0 or 1), and (d) from 0 to 30 mass % of a (meth)acrylic acid ester monomer represented by the following formula (8):

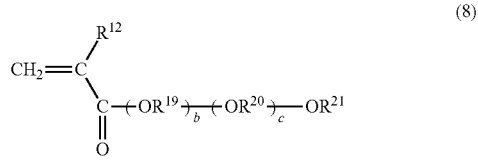

(wherein, $R^{12}$ has the same meaning as described above, $R^{19}$ and $R^{20}$ may be the same or different and each represents an alkylene group having from 2 to 4 carbon atoms, $R^{21}$ represents a hydrogen atom or a methyl group, and b and c each represents a number from 0 to 50 with the proviso that both b and c do not stand for 0).

Examples of the (meth)acrylamide monomer (a) represented by the formula (1) in (B1) include N-n-butyl (meth)acrylamide, N-tert-butyl (meth) acrylamide, N-octyl (meth) acrylamide, N-lauryl (meth)acrylamide, N-1-methylundecyl (meth) acrylamide, N-2-ethylhexyl (meth)acrylamide, and N-tert-octyl (meth)acrylamide. Of these, N-(branched alkyl) (meth)acrylamides such as N-tert-butyl (meth)acrylamide, N-tert-octyl (meth)acrylamide, and N-2-ethylhexyl (meth) acrylamide are more preferred.

These monomers may be used either alone or in combination in an amount of from 30 to 80 mass %, preferably from 40 to 70 mass % based on whole monomers.

Examples of the (meth)acrylamide monomer (b) represented by the formula (2) include (meth)acrylamide, N-methyl (meth)acrylamide, N-ethyl (meth)acrylamide, N-isopropyl (meth)acrylamide, N,N-dimethyl (meth)acrylamide, and N,N-diethyl (meth)acrylamide. Of these, N-methyl (meth) acrylamide, N-ethyl (meth) acrylamide, N,N-dimethyl (meth)acrylamide, and N,N-diethyl (meth)acrylamide are more preferred.

These monomers may be used either alone or in combination in an amount of from 2 to 50 mass %, preferably from 10 to 35 mass % based on whole monomers.

Examples of the (meth)acrylic acid ester or (meth)acrylamide monomer (c) represented by the formula (3) include N,N-dimethylaminoethyl (meth)acrylate, N,N-diethylamino (meth)acrylate, N,N-dimethylaminopropyl (meth)acrylate, N,N-dimethylaminopropyl (meth) acrylamide, and N,N-diethylaminopropyl (meth) acrylamide.

These monomers may be used either alone or in combination in an amount of from 0 to 30 mass %, preferably from 0 to 10 mass %, more preferably from 0.5 to 5 mass %, each based on whole monomers.

The monomer (d) represented by the formula (4) is a (meth) acrylic acid ester having a polyoxyalkylene chain. In the formula, $R^{11}$ represents a hydrogen atom, an alkyl group having from 1 to 10 carbon atoms, or a phenyl group, preferably a hydrogen atom, an alkyl group having from 1 to 4 carbon atoms, more preferably, a methyl group. Examples of such a (meth)acrylic acid ester monomer (4) include hydroxyethyl (meth)acrylate, hydroxypropyl (meth)acrylate, polyethylene glycol mono(meth)acrylate, polypropylene glycol mono(meth)acrylate, methoxypolyethylene glycol mono (meth)acrylate, methoxypolypropylene glycol mono(meth) acrylate, ethoxypolyethylene glycol mono(meth)acrylate, butoxypolyethylene glycol mono(meth)acrylate, and phenoxypolyethylene glycol mono(meth)acrylate. The polyoxyalkylene chain is a homopolymer or copolymer of a $C_{2-4}$ alkylene oxide. When it is a copolymer, it may be either a block copolymer or random copolymer of ethylene oxide, propylene oxide, or the like. The degree of polymerization of the alkylene oxide can be analyzed by using gas chromatography and it is preferably from 1 to 50 on average.

These monomers may be used either alone or in combination in an amount of from 0 to 40 mass %, preferably from 5 to 30 mass %, more preferably from 10 to 25 mass %, each based on whole monomers.

Preferred examples of the copolymer (B1) include N-tert-butyl (meth) acrylamide/N,N-dimethyl (meth)acrylamide/N, N-dimethylaminopropyl (meth) acrylamide/methoxy polyethylene glycol (meth)acrylate, N-tert-butyl (meth) acrylamide/N,N-dimethyl (meth)acrylamide/N,N-dimethylaminoethyl (meth)acrylate/methoxy polyethylene glycol (meth)acrylate, N-tert-butyl (meth) acrylamide/N-methyl (meth)acrylamide/N,N-dimethylaminoethyl (meth)acrylate/ methoxy polyethylene glycol (meth)acrylate, N-tert-butyl (meth) acrylamide/N-methyl (meth)acrylamide/N,N-dimethylaminopropyl (meth) acrylamide/methoxy polyethylene glycol (meth)acrylate, N-tert-butyl (meth) acrylamide/N,N-dimethyl (meth)acrylamide/N,N-dimethylaminopropyl (meth)acrylamide, N-tert-octyl (meth) acrylamide/N,N-diethyl (meth)acrylamide/N,N-dimethylaminopropyl (meth) acrylamide/methoxy polyethylene glycol (meth)acrylate, N-tert-octyl (meth) acrylamide/N,N-dimethyl (meth)acrylamide/N,N-dimethylaminopropyl (meth) acrylamide/methoxy polyethylene glycol (meth)acrylate, N-tert-butyl (meth) acrylamide/N,N-dimethyl (meth)acrylamide/N,N-dimethylaminopropyl (meth) acrylamide/2-hydroxyethyl (meth) acrylate, and N-tert-butyl (meth) acrylamide/N,N-diethyl (meth) acrylamide/N,N-dimethylaminopropyl (meth) acrylamide/methoxy polyethylene glycol(meth)acrylate. Of these, N-tert-butyl (meth)acrylamide/N,N-dimethyl (meth)acrylamide/N,N-dimethylaminopropyl (meth) acrylamide/methoxy polyethylene glycol (meth)acrylate being more preferred.

Examples of the (meth)acrylamide monomer (a) represented by the formula (5) in (B2) include (meth) acrylamide, N-n-butyl (meth) acrylamide, N-tert-butyl (meth) acrylamide, N-octyl (meth) acrylamide, N-lauryl (meth)acrylamide, and (meth)acryloylmorpholine. Of these, N-butyl (meth)acrylamide, N-octyl (meth)acrylamide, and N-lauryl (meth)acrylamide are more preferred.

These monomers may be used either alone or in combination in an amount of from 30 to 80 mass %, preferably from 40 to 70 mass %, based on whole monomers.

Examples of the (meth)acrylic acid ester monomer (b) represented by the formula (6) include methyl (meth)acrylate, ethyl (meth)acrylate, propyl (meth)acrylate, and butyl (meth)acrylate.

These monomers may be used either alone or in combination in an amount of from 5 to 45 mass %, preferably from 10 to 40 mass % based on whole monomers.

Examples of the (meth)acrylic acid ester or (meth)acrylamide monomer (c) represented by the formula (7) include N,N-dimethylaminoethyl (meth)acrylate, N,N-diethylaminoethyl (meth)acrylate, N,N-dimethylaminopropyl (meth) acrylate, N,N-dimethylaminopropyl (meth) acrylamide, and N,N-diethylaminopropyl (meth) acrylamide.

These monomers may be used either alone or in combination in an amount of from 2 to 30 mass %, preferably from 5 to 20 mass % based on whole monomers.

Examples of the (meth)acrylic acid ester monomer (d) represented by the formula (8) include hydroxyethyl (meth)

acrylate, hydroxypropyl (meth)acrylate, polyethylene glycol mono(meth)acrylate, polypropylene glycol mono(meth)acrylate, methoxy polyethylene glycol mono(meth)acrylate, and methoxy polypropylene glycol mono(meth)acrylate. The polyoxyalkylene chain is a homopolymer or copolymer of a $C_{2-4}$ alkylene oxide. When it is a copolymer, it may be either a block copolymer or random copolymer of ethylene oxide, propylene oxide, or the like. The degree of polymerization of the alkylene oxide can be analyzed by using gas chromatography and it is preferably from 1 to 50 on average.

These monomers may be used either alone or in combination in an amount of from 0 to 30 mass %, preferably from 5 to 15 mass %, each based on whole monomers.

Preferred examples of the copolymer (B2) include N-tert-butyl (meth)acrylamide/N,N-dimethylaminopropyl (meth)acrylamide/methoxy polyethylene glycol (meth)acrylate/ethyl (meth)acrylate, N-tert-butyl (meth)acrylamide/N,N-dimethylaminoethyl (meth)acrylate/methoxy polyethylene glycol (meth)acrylate/ethyl (meth)acrylate, N-tert-butyl (meth)acrylamide/N,N-dimethylaminoethyl (meth)acrylate/methoxy polyethylene glycol (meth)acrylate/methyl (meth)acrylate, N-tert-butyl (meth)acrylamide/N,N-diethylaminoethyl (meth)acrylate/methoxy polyethylene glycol (meth)acrylate/ethyl(meth)acrylate, N-tert-butyl (meth)acrylamide/N,N-dimethylaminoethyl (meth)acrylate/2-hydroxyethyl (meth)acrylate/ethyl (meth)acrylate, N-tert-octyl (meth)acrylamide/N,N-dimethylaminoethyl (meth)acrylate/methoxy polyethylene glycol (meth)acrylate/n-butyl (meth)acrylate, N-tert-octyl (meth)acrylamide/N,N-diethylaminoethyl (meth)acrylate/methoxy polyethylene glycol (meth)acrylate/n-butyl (meth)acrylate, and N-tert-butyl (meth)acrylamide/N,N-dimethylaminopropyl (meth)acrylamide/ethyl (meth)acrylate. Of these, N-tert-butyl (meth)acrylamide/N,N-dimethylaminopropyl (meth) acrylamide/methoxy polyethylene glycol(meth)acrylate/ethyl (meth)acrylate is more preferred.

The copolymers (B1) and (B2) can each be prepared by using the monomers described above in combination in accordance with the process described in, for example, JP-A-H08-291206 or JP-A-H02-180911.

The weight-average molecular weight (gel filtration chromatography (relative to polyethylene glycol)) of the copolymer thus obtained can be controlled to from 1,000 to 1,000,000 by selecting the polymerization conditions. In the present invention, the copolymer has preferably a weight-average molecular weight of from 10,000 to 500,000, more preferably from 20,000 to 200,000.

The copolymers thus obtained can be used after neutralization of their tertiary amino group with an inorganic acid or organic acid in order to impart them water solubility. In this case, preferably 50% or more of all the tertiary amino groups are neutralized.

Examples of the inorganic acid include hydrochloric acid, sulfuric acid, and phosphoric acid, while those of the organic acid include acetic acid, glycolic acid, dimethylglycolic acid, lactic acid, dimethylolpropionic acid, tartaric acid, citric acid, maleic acid, and malic acid.

The amino group in the copolymer may be quaternized with an appropriate quaternizing agent. In this case, preferably 50% or more of all the tertiary amino groups are quaternized.

Examples of such a quaternizing agent include dialkyl sulfates such as dimethyl sulfate and diethyl sulfate, alkyl halides such as methyl chloride, propyl bromide, and benzyl chloride, and aralkyl halides.

Such a quaternized copolymer can also be obtained by quaternizing the monomer (3) or (7) with a quaternizing agent, followed by copolymerization.

Poly(N-acylalkyleneimine)-modified silicones are also usable as the film-forming polymer to be used in the aerosol hair cosmetic composition. The poly(N-acylalkyleneimine)-modified silicones are preferably those having, in the molecule thereof, a poly(N-acylalkyleneimine) segment composed of repeating units represented by the following formula (9a):

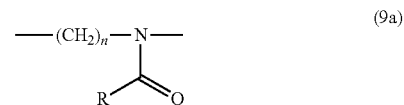

(wherein, R represents a hydrogen atom, an alkyl group having from 1 to 12 carbon atoms, a cycloalkyl group, an aralkyl group, or an aryl group and n represents 2 or 3) and an organopolysiloxane segment, in which the poly(N-acylalkyleneimine) segment composed of repeating units represented by the formula (9a) has been coupled to at least one silicon atom of the end or side chain of the organopolysiloxane segment via a hetero-containing alkylene group. The poly(N-acylalkyleneimine)-modified silicone contains the poly(N-acylalkyleneimine) segment and the organopolysiloxane segment at a mass ratio of preferably from 1/50 to 20/1, more preferably from 1/40 to 20/1 and has a molecular weight of preferably from 500 to 500,000, more preferably from 1,000 to 300,000. In addition, R represents preferably a methyl or ethyl group.

Examples of the hetero-containing alkylene group via which the poly(N-acylalkyleneimine) segment has been coupled to at least one silicon atom of the end or side chain of the organopolysiloxane segment include alkylene groups having from 2 to 20 carbon atoms and containing from 1 to 3 atoms selected from nitrogen atoms, oxygen atoms and sulfur atoms, with alkylene groups having from 2 to 5 carbon atoms and containing a nitrogen atom being more preferred.

Preferred examples of such a poly(N-acylalkyleneimine)-modified silicones include poly(N-formylethyleneimine)-modified silicone, poly(N-acetylethyleneimine)-modified silicone, and poly(N-propionylethyleneimine)-modified silicone. Of these, poly(N-propionylethyleneimine)-modified silicone (INCI name: Polysilicone-9 (product of Kao)) having a weight-average molecular weight of about 20,000 to 200,000 and having, in the molecule thereof, a poly(N-propionylethyleneimine) segment in an amount of from about 3 to 50 mass % is preferred.

The poly(N-acylalkyleneimine)-modified silicones can be prepared by the known process, for example, the process described in JP-A-H07-133352 and can be synthesized, for example, in the following manner. First, the poly(N-acylalkyleneimine) segment composed of repeating units represented by the above formula (9a) is available by cationic ring-opening polymerization of a cyclic iminoether compound represented by the following formula (9b):

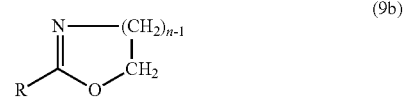

The cyclic iminoethers can be prepared, for example, in accordance with the method described in Liebigs Ann. Chem., 996-1009 (1974). As a monomer for ring-opening polymerization, the cyclic iminoethers may be used either alone or in combination of two or more thereof.

Examples of a polymerization initiator for the ring-opening polymerization of the cyclic iminoether include, but not limited to, alkyl toluenesulfonates, dialkyl sulfates, alkyl trifluoromethanesulfonates, and alkyl halides. These initiators may be used either alone or as a mixture.

A molecular chain of the poly(N-acylalkyleneimine) can be obtained by ring-opening polymerization of the cyclic iminoether compound represented by the formula (9b) in the presence of such an initiator. The molecular chain may be either a single polymer chain or a copolymer chain. The copolymer chain may be either a random copolymer chain or a block copolymer chain.

The molecular chain of the poly(N-acylalkyleneimine) has a molecular weight of preferably from 150 to 50,000, more preferably from 500 to 10,000.

The modified silicone to be used in the present invention can be obtained by reacting a polymerization active species obtained by the ring-opening polymerization of the cyclic iminoether compound represented by the formula (9b) and an organopolysiloxane having a functional group reactive with the polymerization active species.

Examples of the functional group reactive with the polymerization active species include primary amino groups, secondary amino groups, tertiary amino groups, a mercapto group, a hydroxyl group, and a carboxylate group. Of these, amino groups are preferred. The organopolysiloxane having, in the molecule thereof, an amino group has a molecular weight of preferably from 300 to 400,000, more preferably from 800 to 250,000.

The reaction between the amino-containing organopolysiloxane and the reactive end of the poly(N-acylalkyleneimine) obtained by the cationic polymerization of the cyclic iminoether can be effected in the following manner.

Dissolve the initiator in a polar solvent, preferably a solvent composed solely of acetonitrile, valeronitrile, dimethylformamide, dimethylacetamide, chloroform, methylene chloride, ethylene chloride, ethyl acetate, or methyl acetate, or a mixed solvent with another solvent if necessary; and heat the resulting solution to from 40 to 150° C., preferably to from 60 to 100° C. Charge the cyclic iminoether represented by the formula (9b) at once or if the reaction is severe, it is added dropwise to perform polymerization. The progress of the polymerization can be followed by determining the remaining amount of the monomer, that is, the cyclic iminoether by using an analytical instrument such as gas chromatography. Even after the cyclic iminoether is consumed and polymerization is completed, the active species at the growing end still keeps its reactivity. Without isolating the polymer, successively mix the resulting polymer solution with an organopolysiloxane having, in the molecule thereof, an amino group and react the resulting mixture at from 5 to 100° C., preferably at from 20 to 60° C. Their mixing ratio can be selected desirably as needed, but it is preferred to react from 0.1 to 1.3 mols of the poly(N-acylalkyleneimine) with 1 mol of the amino group in the organopolysiloxane.

A block copolymer or graft polymer having the poly(N-acylalkyleneimine) segment bonded to the polydimethylsiloxane can be obtained.

The aerosol hair cosmetic composition (B) may contain one or more film-forming polymers. It is preferred that the composition contains preferably two or more polymers selected from the above-described film-forming polymers, more preferred that all of them are selected from the above-described film forming polymers. The content of the film-forming polymer(s) in the stock solution of the hair cosmetic composition (which will equally apply hereinafter) is preferably from 0.6 to 24 mass %, more preferably from 1.3 to 20 mass %, even more preferably from 2 to 16 mass % from the standpoints of high styling performance, wash-off property with a shampoo, good feel, and balance in compatibility with a propellant.

The hair cosmetic composition may further contain ethanol and/or water. The content of it or them in the stock solution is preferably from 70 to 99 mass %, more preferably from 80 to 97 mass %, even more preferably from 85 to 95 mass % from the standpoint of improving the solubility of the copolymer or plasticizer contained in the cosmetic composition and the sprayed state.

Some of solvents or nonionic surfactants soften the film-forming polymer and reduce the breaking strength (they may usually be called "plasticizer"). Examples of such solvents include solvents having three or more carbon atoms and having, in the molecule thereof, a hydroxyl group, ester solvents, N-hydroxyethylcarboxylic acid amides, and nonionic surfactants.

Specific examples of the solvent having 3 or more carbon atoms and having, in the molecule thereof, a hydroxyl group include monohydric alcohols such as propanol, butanol, benzyl alcohol, ethoxyethyl alcohol, and phenoxyethanol and polyhydric alcohols such as propylene glycol, 1,3-butylene glycol, glycerin, isopentyl glycol, hexylene glycol, dipropylene glycol, polypropylene glycol (degree of polymerization: 9), and polyethylene glycol 600.

Examples of the ester oils include fatty acid triglycerides such as (caprylic/capric) triglyceride and oleic acid triglyceride, fatty acid esters of a divalent alcohol such as neopentyl glycol dipalmitate and dipentaerythrityl (hydroxystearate/stearate/rosinate), and fatty acid esters of a monohydric alcohol such as isopropyl myristate.

Examples of the N-hydroxyethylcarboxylic acid amide include N-acetylethanolamide.

Examples of the nonionic surfactant include fatty acid monoglycerides such as oleic acid monoglyceride and caprylic acid monoglyceride; fatty acid diethanolamides such as palm kernel fatty acid diethanolamide; sorbitan fatty acid esters such as sorbitan monooleate and sorbitan monolaurate; polyoxyalkylene sorbitan fatty acid esters such as polyoxyethylene sorbitan trioleate, polyoxyethylene sorbitan monooleate, polyoxyethylene sorbitan monostearate, and polyoxyethylene sorbitan monopalmitate; alkyl glyceryl ethers such as isostearyl glyceryl ether and isodecyl glyceryl ether; fatty acid polyoxyethylene sorbitols such as polyoxyethylene sorbitol tetraoleate and polyoxyethylene sorbitol tetraoleate; and polyoxyalkylene alkyl ethers such as polyoxyethylene (9) tridecyl ether and polyoxyethylene (9) lauryl ether.

From the standpoint of improving, if the film-forming polymer forms a fragile film, the fragility of the film, while keeping a high breaking strength, the content of the above-described solvent or nonionic surfactant in the stock solution is preferably from 0 to 5 mass %, more preferably from 0 to 2 mass %, even more preferably from 0 to 1 mass %, even more preferably 0%.

The hair cosmetic composition may contain various components used in ordinary cosmetic compositions such as cationic surfactants, anionic surfactants, nonionic surfactants other than those described above, amphoteric surfactants, pH regulators, vitamin preparations, proteins, amino acids, crude drugs, antiseptics, ultraviolet absorbers, antioxidants, and colorants, depending on the intended use.

The hair cosmetic composition, together with a propellant, constitutes an aerosol hair cosmetic composition.

A mass ratio of components other than a propellant (which will hereinafter be called "stock solution") and the propellant, that is, (stock solution)/(propellant), is preferably from 70/30 to 30/70, more preferably from 60/40 to 40/60 in order to achieve good workability and to obtain sufficient styling performance.

The aerosol hair cosmetic composition can be prepared by filling a pressure container with the stock solution and a propellant. The aerosol hair cosmetic composition may be any of hair foam, hair mousse (foam), or hair spray (mist), but hair spray is preferred.

The stock solution having a viscosity at 30° C. of 15 mPa·s or less, further 10 mPa·s or less is preferred in order to spray the stock solution as fine droplets. The term "viscosity" as used herein means a value measured by using a Brookfield viscometer (Rotor with BL adapter, rotation speed at 30 rpm, for 60 seconds at 30° C.)

Examples of the propellant include liquefied natural gas (LPG), dimethyl ether (DME), carbon dioxide gas, nitrogen gas, and mixtures thereof. Alternatives for chlorofluorocarbon such as HFC-152a may also be used.

The pressure in the pressure container is preferably adjusted to from 0.12 to 0.45 MPa at a temperature of 25° C. from the standpoint of achieving good spraying property and good adhesion property.

A valve to be used for the pressure container has preferably a stem hole diameter Ø of from 0.33 to 0.46 mm and a housing bottom hole diameter Ø of from 0.33 to 0.65 mm×a vapor tap diameter Ø of from 0 to 0.64 mm. In a water-containing formulation, the valve has more preferably a stem hole diameter Ø of from 0.33 to 0.42 mm and a housing bottom hole diameter Ø of from 0.33 to 0.42 mm and has no vapor tap, while in a non-aqueous formulation, the valve has more preferably a stem hole diameter Ø of from 0.40 to 0.46 mm and a housing bottom hole diameter Ø of from 0.42 to 0.65 mm×a vapor tap hole diameter Ø of from 0.33 to 0.46 mm.

The hair cosmetic composition, when sprayed from the container, forms liquid droplets having an average particle size of preferably from 10 to 60 μm, more preferably from 15 to 50 μm, even more preferably from 20 to 40 μm from the standpoint of balance among hair styling performance, retention prior to application of the composition, and time until the hair is fixed.

The term "average particle size" as used herein means 50% of the cumulative volume distribution as measured (measurement distance: 15 cm) by spraying the solution directly to a laser light at a measuring range R4 (focus distance: 200 mm, particle size measuring range from 0.5/1.8 to 350 μm) by using a laser diffraction particle size distribution analyzer "HELOS SYSTEM" manufactured by Sympatec GmbH, system-Partikel-technik.

Although a method of applying the aerosol hair cosmetic composition (B) to hair is not limited, it is preferred to spray from a position at least 10 cm apart from the hair, not to continue spraying the composition for one second or greater to the same position (to spray uniformly by moving the container), or the like to prevent application of a large amount of the composition to a specific place, thereby improving the hair feel.

In the present invention, the step (A) of increasing the number of intersections of hair fibers to enhance the volume of the hair may be followed by the step (B) of applying the aerosol hair cosmetic composition to the hair or the step of (B) of applying the aerosol hair cosmetic composition to the hair may be followed by the step (A) of increasing the number of intersections of hair fibers to enhance the volume of the hair. Of these, the former one, that is, the step (A) of increasing the number of intersections of hair fibers to enhance the volume of the hair is followed by the step (B) of applying the aerosol hair cosmetic composition to the hair, is preferred because it facilitates backcombing and in addition, is effective for forming a hair style promptly and keeping the hair style thus formed.

By styling the hair in such a manner, it is possible to cause hair fibers to adhere to each other while crossing them and keep a fluffy hair style for long hours.

As one example of the aerosol hair cosmetic compositions more suited in the hair styling method according to the present invention (which will hereinafter be called "hair cosmetic composition according to the present invention"), there can be exemplified an aerosol hair cosmetic composition containing (C) at least one copolymer selected from (C1) and (C2) and (D) an anionic film-forming polymer at (D)/(C) mass ratio of from 0.1 to 100.

The component (C) used in the hair cosmetic composition according to the present invention is the same as the at least one copolymer selected from (B1) and (B2) described above (in the description of the hair cosmetic composition according to the present invention, (B1) and (B2) correspond to (C1) and (C2), respectively).

As the copolymer of the component (C), at least one selected from (C1) and (C2) can be used. It is contained, in the stock solution of the aerosol hair cosmetic composition, in an amount of preferably from 0.1 to 12 mass %, more preferably from 0.3 to 10 mass %, even more preferably from 0.5 to 8 mass % in order to achieve high hair styling performance.

As the component (D) to be used in the hair cosmetic composition according to the present invention, those described above as the anionic film-forming polymer can be used. The term "film-forming polymer" as used herein has the same meaning as defined above.

As the component (D), at least one film-forming polymer can be used. From the standpoint of achieving both high hair styling performance and non-coarseness, the content of it in the stock solution of the aerosol hair cosmetic composition is preferably from 0.5 to 12 mass %, more preferably from 1 to 10 mass %, even more preferably from 1.5 to 8 mass %.

The component (C) and the component (D) are contained at a (D)/(C) mass ratio of preferably from 0.1 to 100, more preferably from 0.25 to 20, even more preferably from 0.4 to 10, even more preferably from 1 to 5 from the standpoints of high hair styling performance, high wash-off property, non-coarseness, non-stickiness, less whitening, and compatibility balance with a propellant. The term "whitening" as used herein means a phenomenon that when the aerosol hair cosmetic composition is sprayed to the hair, hair seems white due to the irregular reflection of light caused by air bubbles contained in the composition applied to the hair.

The hair cosmetic composition according to the present invention may further contain, as a component (E), a poly(N-acylalkyleneimine)-modified silicone. It is preferred because it can reduce the coarseness or stickiness of the hair to which the composition has been applied, and can provide adequate slip properties. As the poly(N-acylalkyleneimine)-modified silicone as the component (E), those similar to the poly(N-acylalkyleneimine)-modified silicones described above can be exemplified.

As the component (E), one or more of them can be used. The content of it (them) in the stock solution of the aerosol hair cosmetic composition is preferably from 0.01 to 3 mass %, more preferably from 0.04 to 1 mass %, even more preferably from 0.06 to 0.5 mass % from the standpoint of simultaneously satisfying sufficient hair styling performance, non-coarseness, non-stickiness, and high slip properties.

The hair cosmetic composition according to the present invention may further contain ethanol and/or water. The content of it (them) in the stock solution is preferably from 70 to 99 mass %, more preferably from 80 to 97 mass %, even more preferably from 85 to 95 mass % from the standpoint of improving the solubility of the copolymer or plasticizer contained in the cosmetic composition or the sprayed state.

It is possible to add a solvent or nonionic surfactant similar to those described above from the standpoint of improving, if the film-forming polymer forms a fragile film, the fragility of the film while keeping a high breaking strength of the film forming polymer. The content of the solvent or nonionic surfactant in the stock solution is preferably from 0 to 5 mass %, more preferably from 0 to 2 mass %, even more preferably from 0 to 1 mass %, even more preferably 0%.

The hair cosmetic composition according to the present invention may contain various components used in conventional hair cosmetic compositions such as cationic surfactants, anionic surfactants, nonionic surfactants other than those described above, amphoteric surfactants, pH regulators, vitamin preparations, proteins, amino acids, crude drugs, antiseptics, ultraviolet absorbers, antioxidants, and colorants, depending on the intended use.

The hair cosmetic composition, together with a propellant (F), constitutes the aerosol hair cosmetic composition of the present invention.

A mass ratio of components other than the component (F) (which components will hereinafter be called "stock solution") and the component (F), that is, a (stock solution)/(F) mass ratio, is preferably from 70/30 to 30/70, more preferably from 60/40 to 40/60 in order to improve workability and achieve sufficient hair styling performance.

The viscosity of the stock solution, kind of the propellant, pressure of the pressure container, valve used in the pressure container, and average particle size of liquid droplets when they are sprayed from the container are all similar to those described above.

EXAMPLES

In the synthesis examples described below, the content of an organopolysiloxane segment means a value determined from proton nuclear magnetic resonance ($^1$H-NMR) spectrum and the weight-average molecular weight of the final product is a calculated value. The molecular weight of poly (N-propionylethyleneimine) is a number-average molecular weight determined by gel permeation chromatography (GPC).
Column: K-804L (GPC column, product of Showa Denko), two columns connected in series
Eluent: 1 mmol/L "FARMIN DM20" (product of Kao)/chloroform
Flow rate: 1.0 mL/min
Column temperature: 40° C.
Detector: RI
Amount of sample: 5 mg/mL, 100 μL
Using Polystyrene Standards Synthesis Example 1

Diethyl sulfate (6.5 g, 0.042 mol) and 34.4 g (0.36 mol) of 2-ethyl-2-oxazoline were dissolved in 87 g of dehydrated ethyl acetate and the resulting solution was heated under reflux for 8 hours in a nitrogen atmosphere to synthesize an end-reactive poly(N-propionylethyleneimine). The number-average molecular weight of the product was measured by GPC and was found to be 1300. A 33% ethyl acetate solution of 100 g of side-chain primary aminopropyl-modified polydimethylsiloxane (weight-average molecular weight: 40000, amine equivalent: 2500) was added at a time and the resulting mixture was heated under reflux for 10 hours. The reaction mixture was concentrated under reduced pressure to obtain an N-propionylethyleneimine-dimethylsiloxane copolymer as a pale yellow rubber-like semi-solid (138 g, yield: 98%). The final product had an organopolysiloxane segment content of 71 mass % and had a weight-average molecular weight of 56000. Neutralization titration with hydrochloric acid while using methanol as a solvent showed that no amino group remained.

Synthesis Example 2

In a manner similar to that employed in Synthesis Example 1, poly(N-propionylethyleneimine) having a number-average molecular weight of 2700 was obtained using 0.8 g (0.005 mol) of diethyl sulfate, 12.8 g (0.14 mol) of 2-ethyl-2-oxazoline, and 29 g of dehydrated ethyl acetate. Further, an N-propionylethyleneimine-dimethylsiloxane copolymer was obtained as a pale yellow rubber-like solid (111 g, yield: 98%) by using 100 g of side-chain primary aminopropyl-modified polydimethylsiloxane (weight-average molecular weight: 100000, amine equivalent: 20000). The final product had an organopolysiloxane segment content of 88 mass % and had a weight-average molecular weight of 114000. Neutralization titration with hydrochloric acid while using methanol as a solvent showed that no amino group remained.

Examples 1 to 7, and Comparative Examples 1 to 2

In a manner known per se in the art, hair spray stock solutions shown in Table 1 were prepared. Each of the stock solutions and a propellant were filled in an aerosol container equipped with the below-described valve and button at a stock solution/propellant (mass ratio) shown in Table 1 to obtain an aerosol hair cosmetic composition. The hair cosmetic composition thus obtained was measured for film strength. The composition was used for hair styling and volume retention of it under high humidity was evaluated. The results of the aerosol hair cosmetic compositions thus obtained are collectively shown in Table 1. The evaluation results shown in Table 1 are indicated as an average of five expert panel members.

Valve: stem hole diameter φ: 0.60 mm, housing bottom hole diameter φ: 0.65 mm×vapor tap hole diameter φ: 0.42 mm
Button: orifice diameter φ: 0.50 mm (equipped with mechanical brakeup): (product of Mitani Valve)
(Evaluation Method)
Retention Of Volume Under High Humidity Using, as expert panel members, women who had long hair—more specifically, whose untied bangs reached their lip or chin and untied hair on the side or back of the head reached 30 to 40 cm below their ear lobe—, dyed their hair several times during the past one year, and did not perm their hair for the last two years, evaluation was made according to the following method.

Described specifically, panel members formed a voluminous hair style by themselves in accordance with the below-described procedures (1) to (4), applied the hair spray to be evaluated to their hair, and dried for 30 minutes at normal temperature and humidity while sitting still on a chair. Then, they entered a constant humidity room of 30° C. and 98% RH, spent one hour while sitting still on a chair, and evaluated the retention of the hair style based on the following criteria.

(1) Bend down the head, gather the hair on the side closer to the top of the head than ears, and tie the hair with a rubber band firmly. Then, raise the head and stretch the hair bundle to widen it radially.

(2) Backcomb the tied hair entirely with fingertips to form intersections of hair fibers, thereby volumizing the hair.

(3) Wind the hair tip to the tied portion and make a fluffy hair bun. Fix the wound hair at several positions with pins.

(4) Spray the composition over the entire bun for 3 seconds and to the neckline for 2 seconds. Pat the hair to prevent protrusion of the loose hair.

(Evaluation Criteria)

4: A fluffy and voluminous hair style can be kept throughout the hair style thus made.

3: A very slight decrease in volume can be observed on the top of the bun, but it is negligible and a fluffy and voluminous hair style can be kept throughout the hair style.

2: A modest decrease in volume can be observed on the top or at the periphery of the bun, which leads to a slight decrease in volume throughout the hair style, but it is permissible because it does not impair the beauty of the fluffy hair style.

1: A decrease in volume occurs throughout the hair style and the beauty of the fluffy hair style just made has been lost.

TABLE 1

| Component (mass %) | Examples | | | | | | | Comparative Examples | |
|---|---|---|---|---|---|---|---|---|---|
| | 1 | 2 | 3 | 4 | 5 | 6 | 7 | 1 | 2 |
| (Acrylamide/DMAPA acrylate/methoxy PEG methacrylate) copolymer*[1] | 2.2 | | | 7.4 | 2.1 | 1.2 | | | |
| (Acrylamide/alkyl acrylate/DMAPA acrylate/methoxy PEG methacrylate) copolymer*[2] | | | | 1.8 | | | | | |
| Vinylpyrrolidone/N,N-dimethylaminoethyl methacrylic acid copolymer*[3] | | | | | | | | | 9.2 |
| Acrylates/$C_{1-18}$ alkyl acrylates/$C_{1-8}$ alkylacrylamide copolymer neutralized with 2-amino-2-methyl-1-propyl alcohol*[4] | 7.0 | 9.2 | | | 7.0 | | | | |
| Acrylates/diacetoneacrylamide copolymer neutralized with 2-amino-2-methyl-1-propyl alcohol*[5] | | | 9.2 | | | | | | |
| Methyl vinyl ether/maleic anhydride alkyl half ester copolymer*[6] | | | | | | 5.6 | 9.2 | | |
| Poly(N-acylalkyleneimine)-modified silicone (Synthetic Example 2) | | | | | 0.1 | | | | |
| (Methacryloyloxyethylcarboxy betaine/alkyl methacrylate) copolymer*[7] | | | | | | | | 9.2 | |
| 2-Amino-2-methyl-1-propyl alcohol | | | | | | 2.17 | 3.56 | | |
| Lactic acid | 0.025 | | | 0.241 | 0.024 | 0.014 | | | |
| Ethanol | Balance | Balance | Balance | Balance | Balance | Balance | Balance | Balance | Balance |
| Total (stock solution) | 100 | 100 | 100 | 100 | 100 | 100 | 100 | 100 | 100 |
| LPG (0.20 MPa) | 60 | 60 | 60 | 60 | 60 | 60 | 60 | 60 | 60 |
| Dimethyl ether | 40 | 40 | 40 | 40 | 40 | 40 | 40 | 40 | 40 |
| Total (propellant) | 100 | 100 | 100 | 100 | 100 | 100 | 100 | 100 | 100 |
| Stock solution/propellant (mass ratio) | 50/50 | 50/50 | 50/50 | 50/50 | 50/50 | 50/50 | 50/50 | 50/50 | 50/50 |
| Film strength (gf/cm$^2$) | 1700 | 1700 | 1000 | 2500 | 2700 | >3000 | 1200 | Unmeasurable*[8] | <500*[9] |
| Retention of volume under high humidity | 3.4 | 3.2 | 2.4 | 3.8 | 4.0 | 3.6 | 2.4 | 1 | 1 |

TABLE 2

*[1]: Synthesized in accordance with the process described in JP-A-H08-291206. N-tert-butylacylamide/dimethylacrylamide/dimethylaminopropylacrylamide/methoxy polyethylene glycol (PEG400) methacrylate copolymer <52/25/2/21> (mass ratio)
*[2]: Synthesized in accordance with the process described in JP-A-H02-180911. N-tert-butylacylamide/ethyl acrylate/N,N-dimethylaminopropylacrylamide/polyethylene glycol methacrylate copolymer <55/20/15/10> (mass ratio)
*[3]: "Gafquat 734" (product of IPS Japan)
*[4]: "Plascize L-9909B" (product of Goo Chemical)
*[5]: "Plascize L-9540B" (product of Goo Chemical)
*[6]: "Gantrez ES-425" (product of GAF)
*[7]: "Yukaformer M-75" (product of Mitsubishi Chemical)
*[8]: Unmeasurable because of cracks formed during film formation
*[9]: Unmeasurable because of failure in film formation under high humidity Examples 8 to 16, and Comparative Examples 3 to 7

In a manner known per se in the art, hair spray stock solutions having the composition shown in Table 4 or Table 5 were prepared and each of the resulting stock solutions and a propellant were filled in an aerosol container equipped with the below-described vale and button at a stock solution/propellant (mass ratio) shown in Table 4 or Table 5 to prepare aerosol hair cosmetic compositions. The hair cosmetic compositions thus obtained were evaluated for hair styling performance, wash-off property, non-coarseness, non-stickiness, less whitening, and humidity resistance. The results are shown collectively in Tables 4 and 5. The evaluation results in these tables are indicated using a total of ten expert panel members.

Valve: stem hole diameter $\phi$: 0.65 mm, housing bottom hole diameter $\phi$: 0.65 mm×vapor tap hole diameter $\phi$: 0.42 mm Button: orifice diameter $\phi$: 0.50 mm (equipped with mechanical brakeup): (product of Mitani Valve)

(Evaluation Method)

(I) Hair styling performance:

Ten expert panel members made an organoleptic evaluation using a wig ("No. 775S" (implanted after arranged at the root), product of Beaulax) and each hair spray.

Described specifically, apply 5 g of each hair spray to the wig which has been volumized by a beautician in accordance with the procedures (1) to (4) described below and allow the resulting wig to stand at 25° C. and 50% Rh for 30 minutes. Then, fix the wig to a shaker ("ALMIGHTY SHAKER AS-1N", product of ASONE) at 25° C. and 50% Rh, shake it for 6 hours in a vertical direction (180 rpm, amplitude: 4 cm), and evaluate the retention of the hair style in accordance with the below-described criteria.

(1) Bend down the head, gather the hair on the side closer to the top of the head than ears, and tie the hair with a rubber band firmly. Then, raise the head and stretch the hair bundle to widen it radially.

(2) Backcomb the tied hair entirely with fingertips to form intersections of hair fibers, thereby volumizing the hair.

(3) Wind the hair tip to the tied portion and make a fluffy hair bun. Fix the wound hair at several positions with pins.

(4) Spray the composition over the entire bun for 3 seconds and to the neckline for 2 seconds, keeping 15 cm apart from the hair. Pat the hair to prevent protrusion of the loose hair.

(Evaluation criteria)

5: A fluffy and voluminous hair style can be kept throughout the hair style thus made.

4: A very slight decrease in volume can be observed on the top of the bun, but it is negligible and a fluffy and voluminous hair style can be kept throughout the hair style.

3: A modest decrease in volume can be observed on the top or at the periphery of the bun, which leads to a slight decrease in volume throughout the hair style, but it is permissible because it does not impair the beauty of the fluffy hair style.

2. A modest decrease in volume can be observed on the top or at the periphery of the bun, which leads to a decrease in volume throughout hair style, and the beauty of the fluffy hair style has been lost a little.

1: A decrease in volume occurs throughout the hair style and the beauty of the fluffy hair style just made has been lost completely.

(II) Wash-off property:

Ten expert panel members styled their own hair by using each hair spray and organoleptically evaluated the wash-off property upon shampooing in accordance with the below-described criteria.

The experts formed a voluminous hair style on their own head in accordance with the below-described procedures (1) to (4), applied each hair spray, and dried the hair at normal temperature and humidity, more specifically, 25° C. and 50% RH, for two hours while sitting still on a chair. Then, they shampooed their hair with a shampoo for evaluation (refer to Table 3 below) and made a wet-time evaluation during rinsing. After towel drying, they hand-dried with a drier and made a dry-time evaluation when the hair was completely dried. The wash-off property was evaluated in accordance with the following criteria:

(1) Bend down the head, gather the hair on the side closer to the top of the head than ears, and tie the hair with a rubber band firmly. Then, raise the head and stretch the hair bundle to widen it radially.

(2) Backcomb the tied hair entirely with fingertips to form intersections of hair fibers, thereby volumizing the hair.

(3) Wind the hair tip to the tied portion so as not to collapse the volumized hair and make a fluffy hair bun. Fix the wound hair at several positions with pins.

(4) Spray the composition over the entire bun for 3 seconds and to the neckline for 2 seconds. Pat the hair to prevent protrusion of the loose hair.

TABLE 3

| (Composition of shampoo for evaluation) | |
|---|---|
| (Component) | (mass %) |
| Lauramide DEA | 1.5 |
| Sodium laureth sulfate | 15.5 |
| Lauramide DEA | 1.5 |
| Sodium benzoate | 0.5 |
| EDTA-2Na | 0.3 |
| Sodium hydroxide | 0.06 |
| Phosphoric acid | 0.02 |
| Purified water | Balance |
| Total | 100 |

(Evaluation Standards)

5: The hair to which the hair spray has been applied has the same feel as the hair to which no hair spray has been applied both upon wetting after shampooing and upon drying, and it is free from a feel of hair bundle.

4: The hair to which the hair spray has been applied has no frictional feel upon wetting after shampooing but has a slight frictional feel upon drying, compared with the hair to which no spray has been applied, and it is free from a feel of hair bundle.

3: The hair to which the hair spray has been applied has a frictional feel compared with the hair to which no spray has been applied, both upon wetting after shampooing and upon drying, but it is free from a feel of hair bundle.

2: The hair to which the hair spray has been applied has apparently a frictional feel compared with the hair to which no spray has been applied, upon wetting after shampooing and upon drying, and it is not free from a feel of hair bundle.

1: The hair to which the hair spray has been applied has apparently a frictional feel compared with the hair to which no spray is applied, during wetting after shampooing and during drying, is not free from a feel of hair bundle, and in addition, has a white residue on the hair.

(III) Non-stickiness:

Ten expert panel members styled their own hair by using each hair spray and organoleptically evaluate the non-stickiness based on the below-described criteria.

Described specifically, they made a volumized hair style in a manner similar to that employed in the evaluation of the wash-off property (II), applied each hair spray to the hair, and dried thus-treated hair at 25° C. and 50% Rh for 30 minutes while sitting still on a chair. Then, they touched the hair with the surface of their hands and evaluated the non-stickiness based on the following criteria:
(Evaluation Criteria)
5: The hair to which the hair spray has been applied has the same feel as the hair to which no hair spray has been applied.
4: The hair slightly sticks to the hands but is separated soon and the hands do not become sticky.
3: The hair sticks to the hands but the hands do not become sticky.
2: The hair sticks to the hands and the hands also become slightly sticky.
1: The hair sticks to the hands and the hands also become sticky.
(IV) Non-coarseness:
Ten expert panel members styled their own hair by using each hair spray and organoleptically evaluated their non-coarseness based on the below-described criteria.
Described specifically, they made a volumized hair style in a manner similar to that employed in the evaluation of the wash-off property (II), applied each hair spray to the hair, and dried thus-treated hair at 25° C. and 50% Rh for 30 minutes while sitting still on a chair. Then, they touched the hair with the surface of their hands and evaluated the non-coarseness based on the following criteria:
(Evaluation Criteria)
5: The hair to which the hair spray has been applied has the same feel as the hair to which no hair spray has been applied.
4: The hair to which the hair spray has been applied has a little coarser feel than the hair to which no hair spray has been applied, but it does not lose its elasticity and is free from a stiff feel.
3: The hair has lost its elasticity a little and seems stiff, but does not have a coarse feel so much.
2: The hair has a stiff feel, has lost its elasticity and therefore undergoes only a small change in hair style, and is coarse.
1: The hair is resistant to change, is obviously stiff, and has a coarse feel.
(V) Resistance to whitening:
Ten expert panel members styled their own hair by using each hair spray and organoleptically evaluated the non-coarseness based on the below-described criteria.
Described specifically, they made a volumized hair style in a manner similar to that employed in the evaluation of the wash-off property (II), applied each hair spray to the hair, observed the thus-treated hair at normal temperature and humidity whether the hair seemed white or not due to air bubbles contained in the composition attached to the hair, and evaluated based on the following criteria:
(Evaluation criteria)
5: Air bubbles disappear immediately after application of the spray and the hair does not seem white.
4: The hair seems white due to air bubbles immediately after the application but whiteness does not remain because the air bubbles disappear at once.
3: The hair seems white due to air bubbles immediately after the application, but the air bubbles disappear in several seconds and whiteness does not remain.
2: The hair seems white due to air bubbles contained in the composition applied to the hair and whiteness remains a little, though it fades away over time.
1: The hair seems white due to air bubbles contained in the composition applied to the hair and whiteness does not disappear and continues remaining clearly.
(VI) Humidity resistance:
Ten expert panel members made an organoleptic evaluation using a wig ("No. 775S" (implanted after arranged at the root), product of Beaulax) and each hair spray.
Described specifically, apply 5 g of each hair spray to the wig which has been volumized by a beautician in accordance with the procedures similar to those employed in the evaluation of the hair styling performance (I) and allow the resulting wig to stand at 25° C. and 50% Rh for 30 minutes. Then, fix the wig to a shaker ("ALMIGHTY SHAKER AS-1N", product of ASONE) at 40° C. and 75% Rh, shake it for one hour in a vertical direction (180 rpm, amplitude: 4 cm), and evaluate the retention of the hair style in accordance with the below-described criteria.
5: A fluffy and voluminous hair style can be kept throughout the hair style thus made.
4: A very slight decrease in volume can be observed on the top of the bun, but it is negligible and a fluffy and voluminous hair style can be kept throughout the hair style.
3: A modest decrease in volume can be observed on the top or at the periphery of the bun, which leads to a slight decrease in volume throughout the hair style, but it is permissible because it does not impair the beauty of the fluffy hair style.
2. A modest decrease in volume can be observed on the top or at the periphery of the bun, which leads to a decrease in volume throughout hair style, and the beauty of the fluffy hair style has been lost a little.
1: A decrease in volume occurs throughout the hair style and the beauty of the fluffy hair style just made has been lost completely.

TABLE 4

| | | Examples | | | | | | |
|---|---|---|---|---|---|---|---|---|
| | Component (mass %) | 8 | 9 | 10 | 11 | 12 | 13 | 14 |
| C | (Acrylamide/DMAPA acrylate/methoxy PEG methacrylate) copolymer*[10] | | 4.90 | 4.20 | 2.10 | | | |
| | (Acrylamide/alkyl acrylate/DMAPA acrylate/methoxy PEG methacrylate) copolymer*[11] | 5.60 | | | | 1.15 | 0.70 | 0.40 |
| | Vinylpyrrolidone/quaternized dimethylaminoethyl methacrylate copolymer*[12] | | | | | | | |
| D | Acrylates/$C_{1-18}$ alkyl acrylates/$C_{1-8}$ alkylacrylamide copolymer neutralized with 2-amino-2-methyl-1-propyl alcohol*[13] | | | 4.90 | 7.00 | 5.40 | | |
| | acrylates/diacetoneacrylamide copolymer neutralized with 2-amino-2-methyl-1-propyl alcohol*[14] | 1.50 | 2.10 | | | | 7.00 | 7.00 |
| | Methyl vinyl ether/maleic anhydride alkyl half ester copolymer*[15] | | | | | | | |
| | Acrylic acid/alkyl acrylate/alkylacrylamide copolymer*[16] | | | | | | | |

TABLE 4-continued

| Component (mass %) | Examples | | | | | | |
|---|---|---|---|---|---|---|---|
| | 8 | 9 | 10 | 11 | 12 | 13 | 14 |
| E Poly(N-acylalkyleneimine)-modified silicone (Synthesis Example 2) | | | 0.10 | 0.10 | 0.08 | | |
| Poly(N-acylalkyleneimine)-modified silicone (Synthesis Example 1) | | | | | | 0.10 | 0.10 |
| 90% Lactic acid aqueous solution | 0.538 | 0.063 | 0.054 | 0.027 | 0.111 | 0.067 | 0.038 |
| Ethanol | Balance | Balance | Balance | Balance | Balance | Balance | Balance |
| Total (stock solution) | 100 | 100 | 100 | 100 | 100 | 100 | 100 |
| (D)/(C) (mass ratio) | 0.27 | 0.43 | 1.17 | 3.33 | 4.70 | 10.0 | 17.50 |
| LPG (0.20 MPa) | | | 60 | 60 | 60 | 60 | 60 |
| LPG (0.27 MPa) | 100 | 100 | | | | | |
| Dimethyl ether | | | 40 | 40 | 40 | 40 | 40 |
| Total (propellant) | 100 | 100 | 100 | 100 | 100 | 100 | 100 |
| Stock solution/propellant (mass ratio) | 50/50 | 50/50 | 50/50 | 50/50 | 50/50 | 50/50 | 50/50 |
| Hair styling performance | 46 | 33 | 45 | 47 | 38 | 44 | 38 |
| Wash-off property | 37 | 47 | 48 | 43 | 44 | 30 | 32 |
| Non-coarseness | 34 | 38 | 42 | 41 | 39 | 36 | 33 |
| Non-stickiness | 35 | 42 | 40 | 47 | 43 | 41 | 41 |
| Resistance to whitening | 38 | 46 | 34 | 41 | 42 | 43 | 43 |
| Humidity resistance | 42 | 33 | 43 | 44 | 44 | 39 | 38 |

TABLE 5

| Component (mass %) | Examples | | Comparative Examples | | | | |
|---|---|---|---|---|---|---|---|
| | 15 | 16 | 3 | 4 | 5 | 6 | 7 |
| C (Acrylamide/DMAPA acrylate/methoxy PEG methacrylate) copolymer*10 | 1.20 | | | | | | |
| (Acrylamide/alkyl acrylate/DMAPA acrylate/methoxy PEG methacrylate) copolymer*11 | | 2.20 | | 0.06 | 7.00 | 9.20 | |
| Vinylpyrrolidone/quaternized dimethylaminoethyl methacrylate copolymer*12 | | | 2.20 | | | | |
| D Acrylates/$C_{1-18}$ alkyl acrylates/$C_{1-8}$ alkylacrylamide copolymer neutralized with 2-amino-2-methyl-1-propyl alcohol*13 | | | | | | | |
| Acrylates/diacetoneacrylamide copolymer neutralized with 2-amino-2-methyl-1-propyl alcohol[14] | | | | 7.00 | 7.00 | 0.50 | 9.20 |
| Methyl vinyl ether/maleic anhydride alkyl half ester copolymer[15] | 5.60 | | | | | | |
| Acrylic acid/alkyl acrylate/alkylacrylamide copolymer*16 | | 7.00 | | | | | |
| E Poly(N-acylalkyleneimine)-modified silicone (Synthesis Example 2) | | | | | | | |
| Poly(N-acylalkyleneimine)-modified silicone (Synthesis Example 1) | | | | 0.70 | 0.70 | 0.70 | |
| 2-Amino-2-methyl-1-propyl alcohol*17 | 2.17 | | | | | | |
| 90% Lactic acid aqueous solution | 0.015 | 0.211 | | 0.006 | 0.673 | 0.884 | |
| Ethanol | Balance | Balance | Balance | Balance | Balance | Balance | Balance |
| Total (stock solution) | 100 | 100 | 100 | 100 | 100 | 100 | 100 |
| (D)/(C) (mass ratio) | 4.67 | 3.18 | 3.186 | 116.67 | 0.07 | — | — |
| LPG (0.20 MPa) | 60 | 60 | 60 | | | | |
| LPG (0.27 MPa) | | | | 100 | 100 | 100 | 100 |
| Dimethyl ether | 40 | 40 | 40 | | | | |
| Total (propellant) | 100 | 100 | 100 | 100 | 100 | 100 | 100 |
| Stock solution/propellant (mass ratio) | 50/50 | 50/50 | 50/50 | 50/50 | 50/50 | 50/50 | 50/50 |
| Hair styling performance | 32 | 36 | 38 | 39 | 38 | 37 | 36 |
| Wash-off property | 34 | 33 | 13 | 16 | 40 | 41 | 16 |
| Non-coarseness | 37 | 31 | 30 | 20 | 35 | 36 | 25 |
| Non-stickiness | 28 | 35 | 37 | 24 | 17 | 15 | 20 |
| Resistance to whitening | 38 | 28 | 19 | 40 | 42 | 48 | 46 |
| Humidity resistance | 31 | 36 | 18 | 29 | 43 | 39 | 29 |

TABLE 6

*10: Synthesized in accordance with the process described in JP-A-Hei 8-291206. N-tert-butylacrylamide/dimethylacrylamide/dimethylaminopropylacrylamide/methoxy polyethylene glycol (PEG400) methacrylate copolymer <52/25/2/21> (mass ratio)

*11: Synthesized in accordance with the process described in JP-A-Hei 2-180911. N-tert-butylacrylamide/ethyl acrylate/N,N-dimethylaminopropylacrylamide/polyethylene glycol methacrylate copolymer <55/20/15/10> (mass ratio)

*12: "Gafquat 734" (product of GAF)
*13: "Plascize L-9909B" (product of Goo Chemical)
*14: "Plascize L-9540B" (product of Goo Chemical)
*15: "Gantrez ES-425" (product of GAF)
*16: "Ultrahold 8" (product of BASF)
*17: "AMP-100" (product of Dow Chemical Japan)

Formulation Examples 1 to 13

In a manner known per se in the art, hair spray stock solutions having the compositions as shown in Tables 7 and 8 were prepared. Each of the resulting hair spray stock solutions and a propellant were filled in an aerosol container similar to that used in Examples 8 to 16 at a stock solution/propellant (mass ratio) shown in Table 7 or 8 to obtain an aerosol hair cosmetic composition.

The hair cosmetic compositions thus obtained were each excellent in hair styling performance, wash-off property, non-stickiness, non-coarseness, resistance to whitening, and humidity resistance.

TABLE 7

| | Component (mass %) | Formulation Examples | | | | | | |
|---|---|---|---|---|---|---|---|---|
| | | 1 | 2 | 3 | 4 | 5 | 6 | 7 |
| C | (Acrylamide/DMAPA acrylate/methoxy PEG methacrylate) copolymer*[10] | 2.10 | 2.10 | 2.10 | 2.10 | | 4.90 | 4.20 |
| | (Acrylamide/alkyl acrylate/DMAPA acrylate/methoxy PEG methacrylate) copolymer*[11] | | | | | 5.60 | | |
| D | Acrylates/$C_{1-18}$ alkyl acrylates/$C_{1-8}$ alkylacrylamide copolymer neutralized with 2-amino-2-methyl-1-propyl alcohol*[13] | 7.00 | 7.00 | 7.00 | 7.00 | | | 4.90 |
| | Acrylates/diacetoneacrylamide copolymer neutralized with 2-amino-2-methyl-1-propyl alcohol*[14] | | | | | 1.50 | 2.10 | |
| | Methyl vinyl ether/maleic anhydride alkyl half ester copolymer*[15] | | | | | | | |
| | Acrylic acid/alkyl acrylate/alkylacrylamide copolymer*[16] | | | | | | | |
| E | Poly(N-acylalkyleneimine)-modified silicone (Synthesis Example 2) | 0.10 | 0.10 | 0.10 | 0.10 | | | 0.10 |
| | Poly(N-acylalkyleneimine)-modified silicone (Synthesis Example 1) | | | | | | | |
| | 90% Lactic acid aqueous solution | 0.027 | 0.027 | 0.027 | 0.027 | 0.538 | 0.063 | 0.054 |
| | Ethanol | Balance | Balance | Balance | Balance | Balance | Balance | Balance |
| | Total (stock solution) | 100 | 100 | 100 | 100 | 100 | 100 | 100 |
| | (D)/(C) (mass ratio) | 3.33 | 3.33 | 3.33 | 3.33 | 0.27 | 0.43 | 1.17 |
| | LPG (0.20 MPa) | 60 | 60 | 30 | 30 | | | |
| | Dimethyl ether | 40 | 40 | 70 | 70 | | | |
| | HFC-152a | | | | | 100 | 100 | 100 |
| | Total (propellant) | 100 | 100 | 100 | 100 | 100 | 100 | 100 |
| | Stock solution/propellant (mass ratio) | 60/40 | 40/60 | 60/40 | 40/60 | 50/50 | 50/50 | 50/50 |

TABLE 8

| | Component (mass %) | Formulation Examples | | | | | |
|---|---|---|---|---|---|---|---|
| | | 8 | 9 | 10 | 11 | 12 | 13 |
| C | (Acrylamide/DMAPA acrylate/methoxy PEG methacrylate) copolymer*[10] | 2.10 | | | | 1.20 | |
| | (Acrylamide/alkyl acrylate/DMAPA acrylate/methoxy PEG methacrylate) copolymer*[11] | | 1.15 | 0.70 | 0.40 | | 2.20 |
| D | Acrylates/$C_{1-18}$ alkyl acrylates/$C_{1-8}$ alkylacrylamide copolymer neutralized with 2-amino-2-methyl-1-propyl alcohol*[13] | 7.00 | 5.40 | | | | |
| | Acrylates/diacetoneacrylamide copolymer neutralized with 2-amino-2-methyl-1-propyl alcohol*[14] | | | 7.00 | 7.00 | | |
| | Methyl vinyl ether/maleic anhydride alkyl half ester copolymer*[15] | | | | | 5.60 | |
| | Acrylic acid/alkyl acrylate/alkylacrylamide copolymer*[16] | | | | | | 7.00 |
| E | Poly(N-acylalkyleneimine)-modified silicone (Synthesis Example 2) | 0.10 | 0.08 | | | | |
| | Poly(N-acylalkyleneimine)-modified silicone (Synthesis Example 1) | | | 0.10 | 0.10 | | |
| | 2-Amino-2-methyl-1-propyl alcohol*[17] | | | | | 2.17 | |
| | 90% Lactic acid aqueous solution | 0.027 | 0.111 | 0.067 | 0.038 | 0.015 | 0.211 |
| | Ethanol | Balance | Balance | Balance | Balance | Balance | Balance |
| | Total (stock solution) | 100 | 100 | 100 | 100 | 100 | 100 |
| | (D)/(C) (mass ratio) | 3.33 | 4.70 | 10.00 | 17.50 | 4.67 | 3.18 |
| | LPG (0.20 MPa) | | | | | | |
| | Dimethyl ether | | | | | | |
| | HFC-152a | 100 | 100 | 100 | 100 | 100 | 100 |
| | Total (propellant) | 100 | 100 | 100 | 100 | 100 | 100 |
| | Stock solution/propellant (mass ratio) | 50/50 | 50/50 | 50/50 | 50/50 | 50/50 | 50/50 |

The invention claimed is:

1. A hair styling method, comprising:
(A) increasing the number of intersections of hair fibers to enhance the volume of hair, and
(B) applying an aerosol hair cosmetic composition capable of forming a film having a film strength, as measured by a film strength evaluation method, of 800 gf/cm² or greater, wherein said hair cosmetic composition comprises components (C) and (D) at a mass ratio (D)/(C) of from 0.25 to 20:
(C) at least one copolymer selected from the group consisting of (C1) and (C2):
(C1) copolymers each composed of:
(a) from 30 to 80 mass % of a (meth)acrylamide monomer represented by formula (1):

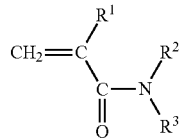
(1)

wherein $R^1$ represents a hydrogen atom or a methyl group, $R^2$ and $R^3$ may be the same or different and each represents a hydrogen atom or an alkyl group having from 4 to 12 carbon atoms, with the proviso that both $R^2$ and $R^3$ do not represent a hydrogen atom,
(b) from 2 to 50 mass % of a (meth)acrylamide monomer represented by formula (2):

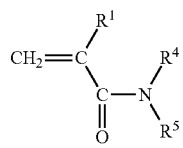
(2)

wherein $R^1$ has the same meaning as defined above, $R^4$ and $R^5$ may be the same or different and each represents a hydrogen atom or an alkyl group having from 1 to 3 carbon atom,
(c) from 0 to 30 mass % of a (meth)acrylic acid ester monomer or a (meth)acrylamide monomer represented by formula (3):

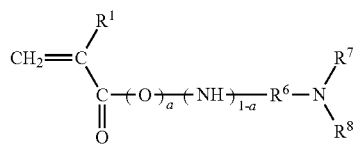
(3)

wherein $R^1$ has the same meaning as defined above, $R^6$ represents an alkylene group having 2 or 3 carbon atoms, $R^7$ and $R^8$ may be the same or different and each represents a methyl group or an ethyl group, and a represents a number of 0 or 1, and (d) from 0 to 40 mass % of a (meth)acrylic acid ester monomer represented by formula (4):

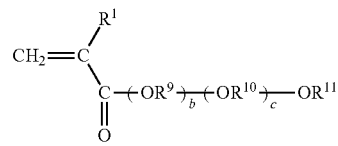
(4)

wherein $R^1$ has the same meaning as defined above, $R^9$ and $R^{10}$ may be the same or different and each represents an alkylene group having from 2 to 4 carbon atoms, $R^{11}$ represents a hydrogen atom, an alkyl group having from 1 to 10 carbon atoms, or a phenyl group, and b and c each represents a number from 0 to 50, with the proviso that both b and c do not stand for 0, and
(C2) copolymers each composed of:
(a) from 30 to 80 mass % of a (meth)acrylamide monomer represented by formula (5):

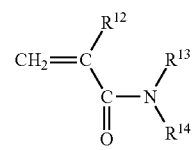
(5)

wherein $R^{12}$ represents a hydrogen atom or a methyl group, $R^{13}$ and $R^{14}$ may be the same or different and each represents a hydrogen atom or an alkyl group having from 4 to 12 carbon atoms or $R^{13}$ and $R^{14}$ are coupled to each other to form a ring together with a nitrogen atom adjacent thereto,
(b) from 5 to 45 mass % of a (meth)acrylic acid ester monomer represented by formula (6):

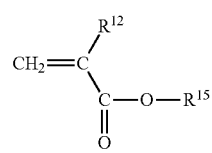
(6)

wherein $R^{12}$ has the same meaning as defined above and $R^{15}$ represents an alkyl group having from 1 to 4 carbon atoms,
(c) from 2 to 30 mass % of a (meth)acrylic acid ester monomer or a (meth)acrylamide monomer represented by formula (7):

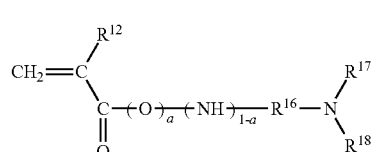
(7)

wherein $R^{12}$ has same the meaning as defined above, $R^{16}$ represents an alkylene group having 2 or 3 carbon atoms, $R^{17}$ and $R^{18}$ may be the same or different and each represents a methyl group or an ethyl group, and a represents a number of 0 or 1, and (d) from 0 to 30 mass % of a (meth)acrylic acid ester monomer represented by formula (8):

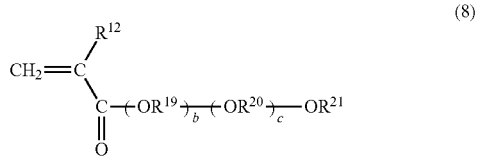

wherein $R^{12}$ has the same meaning as described above, $R^{19}$ and $R^{20}$ may be the same or different and each represents an alkylene group having from 2 to 4 carbon atoms, $R^{21}$ represents a hydrogen atom or a methyl group, and b and c each represents a number from 0 to 50 with the proviso that both b and c do not stand for 0 and (D) an anionic film-forming polymer.

2. The hair styling method according to claim 1, wherein (B) is performed subsequent to (A) and said applying is to the hair.

3. The styling method according to claim 1, wherein said hair cosmetic composition further comprises (E) a poly(N-acylalkyleneimine)-modified silicone.

4. The styling method according to claim 3, wherein component (E) is present at an amount ranging from 0.01 to 3 mass % of the hair cosmetic composition.

5. The styling method according to claim 3, wherein:
component (C) is present at an amount ranging from 0.1 to 12 mass % of the hair cosmetic composition;
component (D) is present at an amount ranging from 0.5 to 12 mass % of the hair cosmetic composition; and
component (E) is present at an amount ranging from 0.01 to 3 mass % of the hair cosmetic composition.

6. The styling method according to claim 5, wherein said hair cosmetic composition comprises from 0 to 5 mass % of a solvent or nonionic surfactant.

7. The styling method according to claim 1, wherein component (C) is present at an amount ranging from 0.1 to 12 mass % of the hair cosmetic composition.

8. The styling method according to claim 1, wherein component (C) is present at an amount ranging from 0.5 to 12 mass % of the hair cosmetic composition.

9. The styling method according to claim 8, wherein said hair cosmetic composition comprises from 0 to 5 mass % of a solvent or nonionic surfactant.

10. The styling method according to claim 1, wherein component (D) is present at an amount ranging from 0.5 to 12 mass % of the hair cosmetic composition.

11. The styling method according to claim 1, wherein said hair cosmetic composition comprises from 0 to 5 mass % of a solvent or nonionic surfactant.

12. The styling method according to claim 1, wherein said hair cosmetic composition comprises 0 mass % of a solvent or nonionic surfactant.

* * * * *